United States Patent
Campbell et al.

(10) Patent No.: US 8,394,325 B2
(45) Date of Patent: *Mar. 12, 2013

(54) MAGNETIC BEADS FOR REDUCING LEUKOCYTE INTERFERENCE IN IMMUNOASSAYS

(75) Inventors: John Lewis Emerson Campbell, Ottawa (CA); Graham Davis, Princeton, NJ (US)

(73) Assignee: Abbott Point of Care Inc., Princeton, NJ (US)

( * ) Notice: Subject to any disclaimer, the term of this patent is extended or adjusted under 35 U.S.C. 154(b) by 337 days.

This patent is subject to a terminal disclaimer.

(21) Appl. No.: 12/815,132

(22) Filed: Jun. 14, 2010

(65) Prior Publication Data
US 2011/0306070 A1 Dec. 15, 2011

(51) Int. Cl.
*G01N 1/00* (2006.01)
*G01N 21/00* (2006.01)

(52) U.S. Cl. .......... 422/73; 422/417; 422/425; 422/430; 422/82.01; 422/82.03; 422/527; 422/554; 435/7.1; 435/7.24; 435/7.32; 435/7.94; 435/287.2; 435/287.9; 436/513; 436/518; 436/523; 436/540; 436/166; 436/175

(58) Field of Classification Search .................. 435/7.1, 435/7.2, 7.24, 7.32, 7.9, 7.92, 7.93, 7.94, 435/287.2, 287.9; 436/506, 512, 513, 518, 436/523, 524, 528, 529, 540, 166, 175, 177; 422/73, 417, 425, 426, 430, 82.01, 82.03, 422/82.11, 527, 554
See application file for complete search history.

(56) References Cited

U.S. PATENT DOCUMENTS

| | | | |
|---|---|---|---|
| 5,063,081 | A | 11/1991 | Cozzette et al. |
| 5,096,669 | A | 3/1992 | Lauks et al. |
| 5,112,455 | A | 5/1992 | Cozzette et al. |
| 5,200,051 | A | 4/1993 | Cozzette et al. |
| 5,447,400 | A | 9/1995 | Seymour |
| 5,554,339 | A | 9/1996 | Cozzette et al. |
| 5,628,961 | A | 5/1997 | Davis et al. |
| 5,656,504 | A | 8/1997 | Johansson et al. |
| 5,821,399 | A | 10/1998 | Zelin |
| 6,030,827 | A | 2/2000 | Davis et al. |
| 6,379,883 | B2 | 4/2002 | Davis et al. |
| 6,911,132 | B2 | 6/2005 | Pamula et al. |
| 7,332,327 | B2 | 2/2008 | Vikholm et al. |
| 7,419,821 | B2 | 9/2008 | Davis et al. |
| 7,682,833 | B2 | 3/2010 | Miller et al. |
| 7,723,099 | B2 * | 5/2010 | Miller et al. ............... 435/287.1 |

(Continued)

FOREIGN PATENT DOCUMENTS

| | | |
|---|---|---|
| EP | 0768530 | 4/1997 |
| WO | WO 00/51814 * | 9/2000 |

(Continued)

OTHER PUBLICATIONS

Barnard et al., J. Chem. Soc. (1966), pp. 227-235.

(Continued)

*Primary Examiner* — Gail R Gabel

(57) ABSTRACT

Methods and devices for reducing interference from leukocytes in an analyte immunoassay are provided. In one embodiment, a method is provided comprising the steps of amending a biological sample with magnetic sacrificial beads opsonized to leukocytes, binding leukocytes in the sample to the magnetic sacrificial beads, and magnetically retaining the beads out of contact from an immunosensor.

21 Claims, 17 Drawing Sheets

U.S. PATENT DOCUMENTS

| | | |
|---|---|---|
| 8,084,272 B2 | 12/2011 | Campbell et al. |
| 2003/0059954 A1 | 3/2003 | Vikholm et al. |
| 2003/0170881 A1 | 9/2003 | Davis et al. |
| 2004/0018577 A1 | 1/2004 | Campbell et al. |
| 2005/0054078 A1 | 3/2005 | Miller et al. |
| 2006/0141450 A1 | 6/2006 | Zhang et al. |
| 2006/0160164 A1 | 7/2006 | Miller et al. |
| 2010/0006706 A1 | 1/2010 | Breitsamter et al. |
| 2010/0167308 A1 | 7/2010 | Miller et al. |
| 2010/0167312 A1 | 7/2010 | Miller et al. |
| 2010/0167386 A1 | 7/2010 | Miller et al. |
| 2010/0173396 A1 | 7/2010 | Miller et al. |
| 2010/0203550 A1 | 8/2010 | Miller et al. |
| 2010/0248273 A1 | 9/2010 | Campbell et al. |
| 2011/0117580 A1 | 5/2011 | Campbell et al. |
| 2011/0117581 A1 | 5/2011 | Campbell et al. |
| 2011/0269159 A1 | 11/2011 | Campbell et al. |
| 2011/0306070 A1 | 12/2011 | Campbell et al. |

FOREIGN PATENT DOCUMENTS

| | | |
|---|---|---|
| WO | WO 2004/053115 | 6/2004 |
| WO | WO 2005/026689 | 3/2005 |
| WO | WO 2011/063010 | 5/2011 |
| WO | WO 2011/063012 | 5/2011 |

OTHER PUBLICATIONS

Wines et al., "The IgC Fc contains distinct Fc receptor (FcR) binding sites: the leukocyte receptors Fc gamma RI and Fc gamma RIIa bind to a region in the Fc distinct from that recognized by neonatal FcR and protein A", Journal of Immunology (Baltimore, MD 1950) May 15, 2000, vol. 164, No. 10, pp. 5313-5318.

International Search Report and Written Opinion for PCT/US2011/040364 mailed Aug. 4, 2011 (14 pages).

Laurell, et al., "Electroimmunoassay", Methods in Enzymology, vol. 73, pp. 339, 340, 346-348. 1981.

M. J. Green Philos. Trans. R. Soc. Lond. B. Biol. Sci., 316: 135-142 (1987).

Hill et al. (FEBS 191, 257-263, 1985).

Ginsberg, et al., "Interaction of Mammalian Cells with Polymorphonuclear Leucocytes", Inflammation, vol. 13 (5): pp. 529-542 (1989).

Isamu Hongo, et al., Phenol-Soluble Modulin a3 Enhances the Human Neutrophil Lysis Mediated by Panton-Valentine Leukocidin, JID, 2009:200 (Sep. 1) pp. 715-723.

Isao Adachi, et al., Heparin-Induced Leukocyte Lysis In Vitro, J. Pharmacobio-Dyn., 9, 207-210 (1986).

Skubitz, et al., Blood 65, pp. 333-339 (1985).

International Search Report and Written Opinion for PCT/US2010/057066 mailed Mar. 1, 2011.

International Preliminary Report on Patentability for PCT/US2010/057062 mailed May 31, 2012.

International Preliminary Report on Patentability for PCT/US2010/057066 mailed May 31, 2012.

International Search Report and Written Opinion for PCT/US2010/057062 mailed Feb. 10, 2011.

International Search Report for PCT/US2011/034121 mailed Jul. 4, 2011.

\* cited by examiner

MAGNETIC BEADS FOR REDUCING LEUKOCYTE INTERFERENCE IN IMMUNOASSAYS

FIELD OF THE INVENTION

The present invention relates to reducing or eliminating interference from buffy coat components, notably leukocytes, in devices and methods for determining the presence or concentration of an analyte in a blood sample by immunoassay. In particular, the invention relates to reducing or eliminating leukocyte immuno sensor interference by amending a blood sample with opsonized magnetic sacrificial beads and similarly opsonized magnetic elements.

BACKGROUND OF THE INVENTION

A multitude of laboratory immunoassay tests for analytes of interest are performed on biological samples for diagnosis, screening, disease staging, forensic analysis, pregnancy testing and drug testing, among others. While a few qualitative tests, such as pregnancy tests, have been reduced to simple kits for a patient's home use, the majority of quantitative tests still require the expertise of trained technicians in a laboratory setting using sophisticated instruments. Laboratory testing increases the cost delay can be detrimental to the patient's condition or prognosis, such as for example the analysis of markers indicating myocardial infarction and heart failure. In these and similar critical situations, it is advantageous to perform such analyses at the point-of-care, accurately, inexpensively and with minimal delay.

Many types of immunoassay devices and processes have been described. For example, a disposable sensing device for successfully measuring analytes in a sample of blood is disclosed by Lauks in U.S. Pat. No. 5,096,669. Other devices for successfully measuring features such as for example clotting time are disclosed by Davis et al. in U.S. Pat. Nos. 5,628,961 and 5,447,440. These devices employ a reading apparatus and a cartridge that fits into the reading apparatus for the purpose of measuring analyte concentrations and viscosity changes in a sample of blood as a function of time. The entire contents and disclosures of U.S. Pat. Nos. 5,096,669; 5,628,961; and 5,447,440 are incorporated herein by reference in their entireties.

U.S. Pat. Appl. Pub. 2006/0160164 to Miller et al. (the "'164 application") describes an immunoassay device with an immuno-reference electrode; U.S. Pat. No. 7,682,833 to Miller et al. describes an immunoassay device with improved sample closure; U.S. Pat. Appl. Pub. 2004/0018577 to Emerson Campbell et al. describes a multiple hybrid immunoassay; and U.S. Pat. No. 7,419,821 to Davis et al. describes an apparatus and methods for analyte measurement and immunoassay, each of which is jointly-owned and incorporated herein by reference in its entirety.

Non-competitive two-site immunoassays, also called sandwich-type immunoassays, are often employed for determining analyte concentration in biological test samples, and are used for example in the point-of-care analyte detection system developed by Abbott Point of Care Inc., the i-STAT® immunoassay system. In a typical two-site enzyme-linked immunosorbent assay (ELISA), one antibody is bound to a solid support to form an immobilized or capture antibody and a second antibody is conjugated or bound to a signal-generating reagent such as an enzyme to form a signal or labeled antibody. Upon reaction with a sample containing the analyte to be measured, the analyte becomes "sandwiched" between the immobilized antibody and the signal antibody. After washing away the sample and any non-specifically bound reagents, the amount of signal antibody remaining on the solid support is measured and should be proportional to the amount of analyte in the sample.

Electrochemical detection, in which the binding of an analyte directly or indirectly causes a change in the activity of an electroactive species adjacent to an electrode, has also been applied to immunoassays. For a review of electrochemical immunoassays, see Laurell et al., Methods in Enzymology, vol. 73, "Electroimmunoassay", Academic Press, New York, 339, 340, 346-348 (1981).

In an electrochemical immuno sensor, the binding of an analyte to its cognate antibody produces a change in the activity of an electroactive species at an electrode poised at a suitable electrochemical potential to cause oxidation or reduction of the electroactive species. There are many configurations or arrangements for meeting these conditions. For example, the electroactive species may be attached directly to an analyte, or the antibody may be covalently attached to an enzyme that either produces an electroactive species from an electroinactive substrate or destroys an electroactive substrate. See, M. J. Green (1987), Philos. Trans. R. Soc. Lond. B. Biol. Sci., 316:135-142, for a review of electrochemical immuno sensors.

The concept of differential amperometric measurement is well known in the electrochemical art. See, for example, jointly-owned U.S. Pat. No. 5,112,455 to Cozzette et al., which is herein incorporated by reference in its entirety. A version of a differential amperometric sensor combination is disclosed in jointly-owned U.S. Pat. No. 5,063,081 to Cozzette et al. (the "'081 patent"), which is also herein incorporated by reference in its entirety. The '081 patent also discloses the use of permselective layers for electrochemical sensors and the use of film-forming latexes for immobilization of bioactive molecules. The use of poly(vinyl alcohol) (PVA) in sensor manufacture is described in U.S. Pat. No. 6,030,827 to Davis et al., which is herein incorporated by reference in its entirety. U.S. Pat. Appl. Pub. 2003/0059954 to Vikholm et al., which is herein incorporated by reference in its entirety, teaches antibodies directly attached to a surface having a biorepellant or biomolecule repellant coating, e.g., PVA, in the gaps between the antibodies on the surface. U.S. Pat. No. 5,656,504 to Johansson et al. teaches a solid phase, e.g., PVA, with antibodies immobilized thereon and is incorporated herein by reference in its entirety, and U.S. Pat. Nos. 6,030,827 and 6,379,883 to Davis et al. teach methods for patterning PVA layers and are incorporated herein by reference in their entireties.

It is well known in the art that immunoassays are susceptible to various forms of interferences. Jointly-owned pending U.S. application Ser. No. 12/411,325 (the "'325 Application"), for example, addresses ameliorating interferences from heterophile antibodies by the inclusion IgM into an IgG reagent cocktail. The '325 application is incorporated herein by reference in its entirety.

As immunoassay technology has increasingly been adapted to enter the point-of-care testing market, the use of whole blood as the test medium has increased relative to plasma and serum, which are generally used in central laboratory testing. When whole blood is analyzed, erythrocytes and buffy coat components are present in the assay medium. Those skilled in the art recognize that the buffy coat is a layer of leukocytes and platelets that forms above the erythrocytes when blood is centrifuged.

It has been found that in certain assays, various assay components, e.g., beads and electrode surfaces, can effectively be opsonized with respect to leukocytes. For example, with respect to an electrode surface, Hill et al. (FEBS 191, 257-263, 1985) opsonized a microvoltammetric electrode with human IgG for the purpose of observing the respiratory burst of a human neutrophil based on electrochemical detection of the superoxide ion.

U.S. Pat. Appl. Pub. 2006/0160164 (the "'164 application"), referenced above, discusses electrochemical immunosensors, the bias between whole-blood and plasma, and provides that immunoassays for markers such as troponin and the like are generally measured and reported as plasma or serum values. The '164 Application teaches that when these immunosensors are used for analysis of whole-blood, either a correction factor or a means for eliminating the bias needs to be employed. The '164 Application further teaches that certain aspects of this bias can be eliminated, including the bias in whole-blood electrochemical immunoassays associated with components of the buffy coat, and also the bias associated with hematocrit variations between samples.

As provided in the '164 Application, leukocyte (or white cell) interference occurs on immunosensors having beads coated with an analyte antibody, e.g., troponin antibody, and control experiments have shown that this positive bias is absent in plasma samples and in blood samples where the buffy coat has been removed. Thus, it appears that leukocytes are able to stick to the immuno sensor and promote non-specific binding of the enzyme-labeled antibodies, which remain bound even after a washing step. In the '164 Application, it was shown that this bias could be partially eliminated by adding a small amount of an antibody to human serum albumin during bead preparation. Consequently, when a sample contacts the modified beads, albumin from the sample rapidly coats the beads and once they are coated with a layer of native albumin the leukocytes should not recognize the beads as an opsonized surface.

The '164 Application describes an additional solution to the leukocyte interference problem wherein the bias is eliminated by increasing the salt concentration of the blood sample from a normal sodium ion concentration of about 140 mM to above about 200 mM, preferably to about 230 mM. The mechanism that accounts for reduced interference may be that the salt causes osmotic shrinkage of the leukocytes. This interpretation is consistent with the leukocytes' impaired ability to interact with the disclosed immunosensor.

Notwithstanding the above literature, the need remains for improved processes for ameliorating effects of leukocyte activity in immunoassays in at least the following areas: immunosensor interference, most notably in the context of point-of-care testing; electrochemical immunoassays; use of an immunosensor in conjunction with an immuno-reference sensor; whole blood immunoassays; single-use cartridge based immunoassays; non-sequential immunoassays with only a single wash step; and dry reagent coatings.

SUMMARY OF THE INVENTION

The invention is directed to reducing or eliminating leukocyte interference in an analyte immunoassay as well as to kits, devices and methods for using such kits and devices.

In a first embodiment, the invention is directed to a method of reducing interference from leukocytes in an analyte immunoassay, comprising contacting a biological sample, e.g., a blood sample, containing leukocytes with magnetic sacrificial beads opsonized to said leukocytes under conditions sufficient to bind at least a portion of said leukocytes in the biological sample to the magnetic sacrificial beads; and magnetically retaining the magnetic sacrificial beads substantially out of contact from an immunosensor. Optionally, the magnetic sacrificial beads comprise a magnetite ($Fe_3O_4$) core coated with a styrene-acrylic acid copolymer or magnetic beads coated with non-human IgG or fragments thereof. The magnetic sacrificial beads preferably have an average particle size of from 0.01 µm to 20 µm, e.g., from 0.1 µm to 5 µm or from 3 µm to 5 µm. Optionally, the magnetic sacrificial beads are in one or more dissolvable dry reagent coatings within an immunoassay cartridge. The magnet may be a permanent magnet or an electromagnet and may be disposed in an immunoassay cartridge or in a reader for an immunoassay cartridge. In preferred aspects at least 50 wt. %, e.g., at least 75 wt. %, of the magnetic sacrificial beads are retained out of contact from the immuno sensor.

In another embodiment, the invention is to a method of performing an analyte sandwich immunoassay in a blood sample, comprising introducing a blood sample containing leukocytes into a holding chamber in a test cartridge, wherein a portion of the holding chamber is coated with magnetic sacrificial beads opsonized to leukocytes; contacting the blood sample with the magnetic sacrificial beads under conditions sufficient to bind at least a portion of the leukocytes in the biological sample to the magnetic sacrificial beads; moving the blood sample into a conduit, wherein a magnetic field localized to at least a portion of the conduit attracts and retains the magnetic sacrificial beads on at least a portion of the wall of the conduit thereby substantially preventing the magnetic sacrificial beads from coming into contact with an immunosensor; contacting the blood sample with the immunosensor to form a sandwich comprising an immobilized capture antibody, a sample analyte and a signal antibody; optionally washing the blood sample from the immunosensor; and detecting the presence of the analyte based on a signal provided by the signal antibody. Optionally, the method further comprises the steps of washing the blood sample from the immunosensor; and contacting the immunosensor with a reagent capable of reacting with said signal antibody to produce the signal at the immunosensor related to the presence of the sample analyte in the blood sample. The analyte optionally is selected from the group consisting of troponin I, troponin T, BNP, creatine kinase MB, procalcitonin, proBNP, NTproBNP, myoglobin and the like, plus other sandwich assays used in clinical diagnostics, e.g., PSA, D-dimer, CRP, HCG, NGAL, myeloperoxidase and TSH. The immobilized capture antibody preferably is attached to a sensor selected from the group consisting of an amperometric electrode, a potentiometric electrode, a conductimetric electrode, an optical wave guide, a surface plasmon resonance sensor, an acoustic wave sensor and a piezoelectric sensor. The immobilized capture antibody may be attached to an assay bead, and the assay bead is attached to an amperometric electrode.

In another embodiment, the invention is to a method of performing an analyte competitive immunoassay in a blood sample, comprising introducing a blood sample containing leukocytes into a holding chamber in a test cartridge, wherein a portion of the holding chamber is coated with magnetic sacrificial beads opsonized to leukocytes; amending the blood sample with a labeled analyte; contacting the blood sample with the magnetic sacrificial beads under conditions sufficient to bind at least a portion of the leukocytes in the biological sample to the magnetic sacrificial beads; applying a magnetic field localized to at least a portion of a conduit to attract and retain the magnetic sacrificial beads on at least a portion of a wall of the conduit thereby substantially preventing the magnetic sacrificial beads from coming into contact with an immunosensor; contacting the blood sample with an immunosensor to form a competitive ratio of bound sample analyte to bound labeled analyte; optionally washing the blood sample from the immunosensor; and detecting the presence of the analyte based on the competitive ratio as determined by a signal provided by the bound labeled analyte. The process optionally further comprises washing the blood sample from the immunosensor; and contacting the immuno sensor with a reagent capable of reacting with the labeled analyte to produce a signal at the immunosensor inversely related to the presence of sample analyte in the blood sample. The sample analyte optionally is selected from the group consisting of digoxin, phenobarbital, phenyloin, theophylline, valproic acid, and vancomycin. The labeled analyte optionally is labeled with a label selected from the group consisting of a radiolabel, an enzyme, a chromophore, a fluorophore, a chemiluminescent species, an ionophore and an electroactive species. For example, the labeled analyte may be labeled with a label selected from the group consisting of a fluorescein, a ferrocene, and a p-aminophenol.

In another embodiment, the invention is to a cartridge for performing a competitive immunoassay for a sample analyte suspected of being present in a blood sample, the cartridge comprising: a sample inlet for receiving the blood sample; a metering chamber for metering the blood sample to form a metered sample; one or more dry reagent coating layers comprising magnetic sacrificial beads opsonized to leukocytes and a labeled analyte; an electrode comprising an immobilized antibody to the sample analyte and to the labeled analyte; and one or more pumping elements for moving the metered sample and the labeled analyte to the electrode. The cartridge may further comprise a magnet for positioning the magnetic sacrificial beads. Alternatively, the magnet may be disposed in the reader device rather than the cartridge In another embodiment, the invention is to a cartridge for performing a non-competitive immunoassay for a sample analyte suspected of being present in a blood sample, the cartridge comprising: a sample inlet for receiving the blood sample; a metering chamber for metering the blood sample to form a metered sample; one or more dry reagent coating layers comprising magnetic sacrificial beads opsonized to leukocytes and a signal antibody to the analyte; an electrode comprising an immobilized antibody to the sample analyte; and one or more pumping elements for moving the metered sample to the electrode. The cartridge may further comprise a magnet for positioning the magnetic sacrificial beads. Alternatively, the magnet may be disposed in the reader device rather than the cartridge.

In another embodiment, the invention is to a kit for performing an analyte immunoassay in a whole blood sample, comprising: magnetic sacrificial beads opsonized to leukocytes, wherein the magnetic sacrificial beads are movable by a magnetic field; optionally a magnet for retaining the magnetic sacrificial beads; and an immunosensor, wherein leukocytes in the whole blood sample are bindable to said magnetic sacrificial beads, and wherein the magnetic field is capable of retaining at least a portion of said magnetic sacrificial beads out of contact from said immunosensor. The immunoassay may be a sandwich assay or a competitive assay.

BRIEF DESCRIPTION OF THE DRAWINGS

These and other objectives, features and advantages of the present invention are described in the following detailed description of the specific embodiments and are illustrated in the following Figures, in which:

FIG. 9($b$) shows an unexpected waveform for a BNP cartridge with a negatively sloping output signal; FIG. 9($c$) shows a normal response, which has a near-zero slope for low analyte concentrations; and FIG. 9($d$) illustrates that negative slopes are expected only at high analyte concentrations where the measurement can become substrate-limited rather than enzyme limited;

DETAILED DESCRIPTION OF THE INVENTION

It has recently been discovered that amending a blood sample with sacrificial beads that have been opsonized for leukocytes reduces leukocyte interference in immunoassays. See U.S. patent application Ser. Nos. 12/620,179 and 12/620, 230, the entireties of which are incorporated herein by reference. The present invention relates to the use of magnetic sacrificial beads to reduce or eliminate interference caused by the presence of leukocytes in immunoassays. In particular, the present invention is directed to a method of reducing interference from leukocytes in an analyte immunoassay, comprising contacting a biological sample containing leukocytes with magnetic sacrificial beads opsonized to said leukocytes under conditions sufficient to bind at least a portion of said leukocytes in the biological sample to the magnetic sacrificial beads, and magnetically retaining the magnetic sacrificial beads substantially out of contact from an immunosensor. In this manner, leukocytes that are bound to the magnetic sacrificial beads are prevented from coming into contact with the immunosensor thereby reducing or eliminating leukocyte interference. As used herein, the term "magnetic" when used to describe sacrificial beads means that the beads are susceptible to movement by a magnetic field or create a magnetic field themselves.

Figure 8:
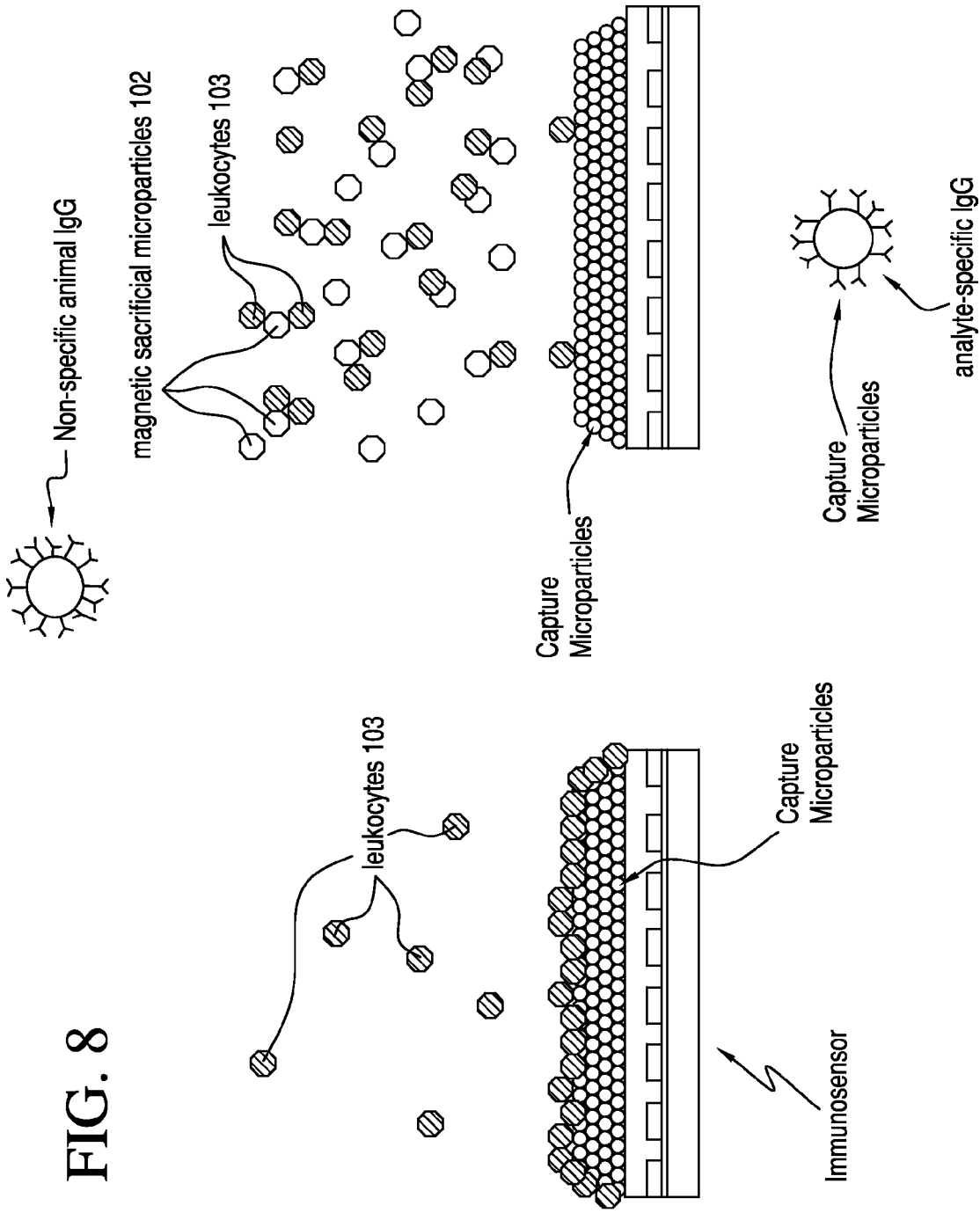
FIG. 8 illustrates the principle of operation of an electrochemical immunosensor with the inclusion of sacrificial beads opsonized for leukocytes.

FIG. 8 illustrates the principle of an amperometric immunoassay for determining the presence and amount of an analyte, e.g., a marker of cardiac function such as BNP and TnI, and employing magnetic opsonized sacrificial beads for reducing leukocyte interference. A fluid sample, e.g., blood sample, is introduced into an immunoassay cartridge and is amended with a dry reagent coated. The dry reagent includes magnetic sacrificial beads 102, which upon dissolution into the sample selectively bind to leukocytes 103 that may be contained in the sample. Once the sacrificial beads have had an opportunity to bind to the leukocytes, a magnetic field is applied to retain the beads in a region substantially out of contact from the immunosensor thereby reducing or eliminating leukocyte interference at the immunosensor.

Thus, in preferred embodiments, the present invention is employed in one or more of the following areas: immunosensors, most notably in the context of point-of-care testing; electrochemical immunoassays; immunosensors in conjunction with immuno-reference sensors; whole blood immunoassays; single-use cartridge based immunoassays; non-sequential immunoassays with only a single wash step; and dry reagent coatings. Notably, while U.S. Pat. Appl. Pub. 2006/0160164 (the "'164 application"), referenced above, addresses certain interferences associated with leukocytes based on the addition of an anti-human serum, albumin antibody coating on an immunosensor, and the addition of salts to the assay medium, the present specification discloses additional sources of bias associated with leukocytes and provides a novel solution for reducing same. As will be appreciated by those skilled in the art, the general concept disclosed herein is applicable to many immunoassay methods and platforms.

Thus, in preferred embodiments, the present invention is employed in one or more of the following areas: immunosensors, most notably in the context of point-of-care testing; electrochemical immunoassays; immunosensors in conjunction with immuno-reference sensors; whole blood immunoassays; single-use cartridge based immunoassays; non-sequential immunoassays with only a single wash step; and dry reagent coatings. Notably, while U.S. Pat. Appl. Pub. 2006/0160164 (the "'164 application"), referenced above, addresses certain interferences associated with leukocytes based on the addition of an anti-human serum, albumin antibody coating on an immunosensor, and the addition of salts to the assay medium, the present specification discloses additional sources of bias associated with leukocytes and provides a novel solution for reducing same. As will be appreciated by those skilled in the art, the general concept disclosed herein is applicable to many immunoassay methods and platforms.

The present invention permits rapid in situ determinations of analytes using a cartridge having an array of analyte sensors and means for sequentially presenting an amended sample to an immunosensor or analyte array. In preferred embodiments, the invention is employed in cartridges that are designed to be operated with a reading device, such as that disclosed in U.S. Pat. No. 5,096,669 to Lauks et al., issued Mar. 17, 1992 (referenced above), or U.S. Pat. No. 7,419,821 to Davis et al., issued Sep. 2, 2008 (referenced above), both of which are incorporated by reference herein in their entireties. The invention is best understood in this context. Consequently, a suitable device and method of operation for a point-of-care immunoassay system is first described, followed by how the system may be best adapted to further reduce or eliminate leukocyte interference in whole blood immunoassays.

In various embodiments, the invention is employed in a heterogeneous electrochemical immunoassay based on the formation of a sandwich at or near the electrode surface. In other embodiments, however, the invention is to other forms of immunoassay. For example, the magnetic sacrificial beads of the present invention may be employed in either heterogeneous or a homogeneous bead-based assays, as well as in non-competitive (sandwich) immunoassays or competitive immunoassays. In this context, the terms "heterogeneous" and "homogeneous" refer to the capture step. Hence, for homogeneous assays, the capture step occurs in the fluid medium, while in heterogeneous assays, the capture step occurs on a macroscopic surface, e.g., sensor surface (in either a competitive or non-competitive manner). In each of these examples, the assay beads will be susceptible to attack by leukocytes when the assay is performed in a blood sample. In competitive and non-competitive assays, this effect can be reduced by the addition of magnetic sacrificial beads opsonized for leukocytes.

Figure 21:
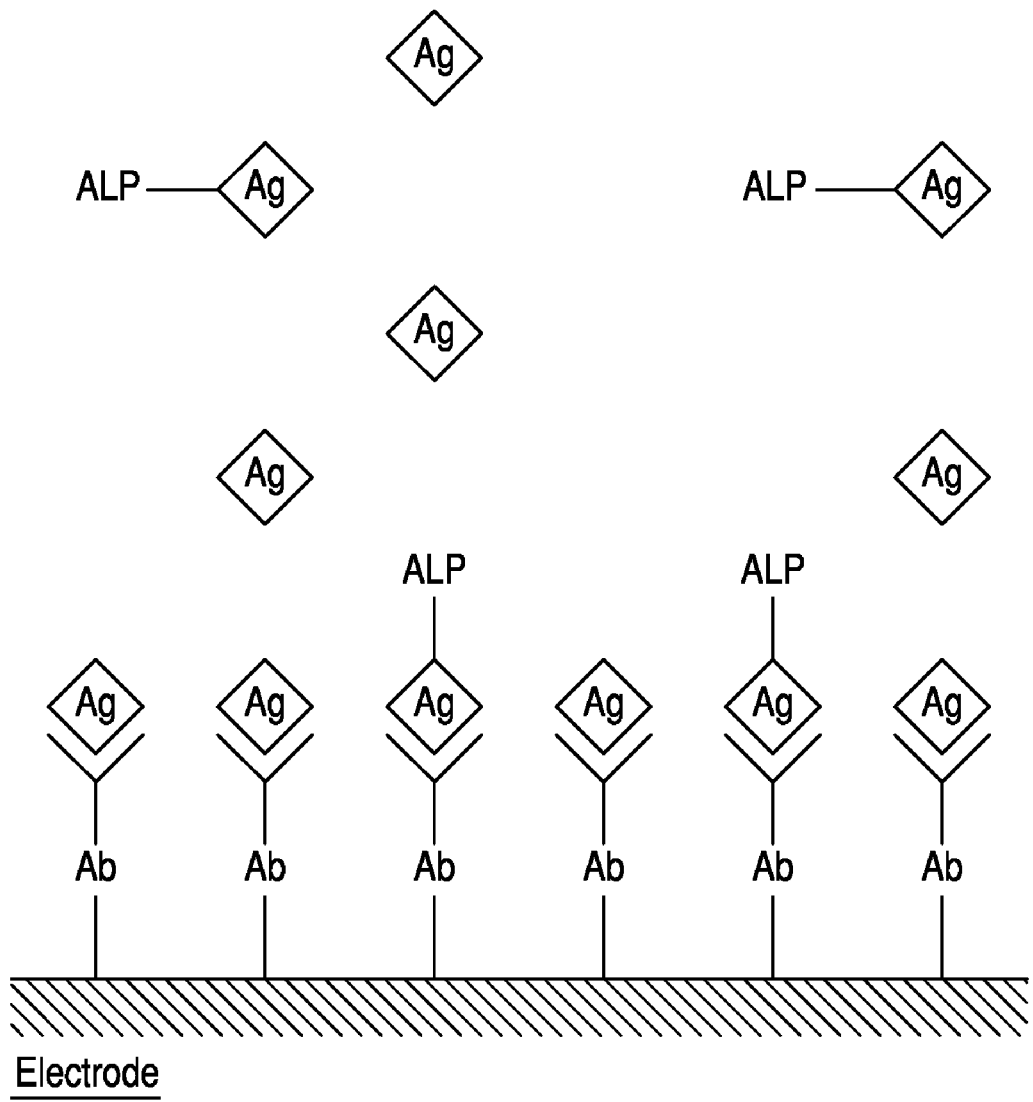
FIG. 21 illustrates a competitive immunoassay, which may be amended with magnetic sacrificial beads according to one embodiment of the invention.

In a heterogeneous competitive assay, illustrated in FIG. 21, an (unlabeled) analyte present in a sample competes with a labeled analyte for binding sites on a solid surface, e.g., a sensor element. A sample suspected of containing the analyte of interest (sample analyte) is amended with a quantity of a reagent comprised of the same analyte conjugated to a label, i.e., the labeled analyte. The label may be a dye or any signal-generating element, such as an enzyme, e.g., ALP. In some exemplary embodiments, the labeled analyte may be labeled with a label selected from the group consisting of a radiolabel, an enzyme, a chromophore, a fluorophore, a chemiluminescent species, an ionophore and an electroactive species. In another embodiment, the labeled analyte is labeled with a label selected from the group consisting of a fluorescein, a ferrocene (optionally a carboxylated ferrocene or dicarboxylated ferrocene or aminoferrocene), and a p-aminophenol.

Analytes commonly identified and/or measured by means of competitive assay include the therapeutic agents such as, for example, digoxin, theophylline and biomarkers such as for example C-reactive protein (CRP) as well as phenobarbital, phenyloin, valproic acid and vancomycin. In preferred embodiments, the sample analyte is selected from the group consisting of digoxin, phenobarbital, phenyloin, theophylline, valproic acid and vancomycin. In one embodiment of the invention, the amended sample is brought into contact with a solid surface on which is immobilized an antibody to the analyte of interest. The sample-borne analyte and the labeled analyte compete for binding at this solid surface so that the amount of labeled analyte and hence the amount of signal generated therefrom will be inversely proportional to the concentration of analyte in the original sample. After washing non-specifically bound material from the sensor surface, the amount of label is measured. In the case of an enzyme label, this would involve supplying a suitable substrate to the enzyme and detecting the product (e.g., electrochemically or optically). When employed in a heterogeneous competitive immunoassay, the blood sample preferably is amended with magnetic sacrificial beads opsonized for leukocytes (e.g., IgG-coated magnetic microparticles) prior to contacting the solid surface, i.e., sensor.

I. Cartridge

Figure 2:
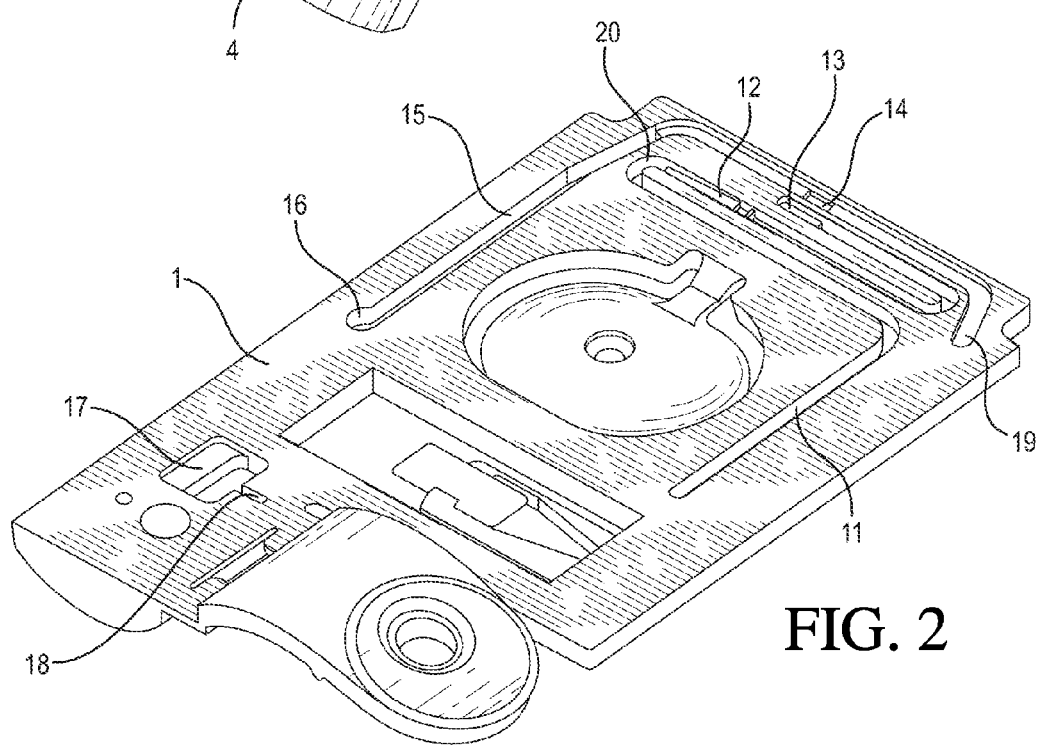
FIG. 2 is an isometric bottom view of an immunosensor cartridge cover of one embodiment of the invention.
Figure 3:
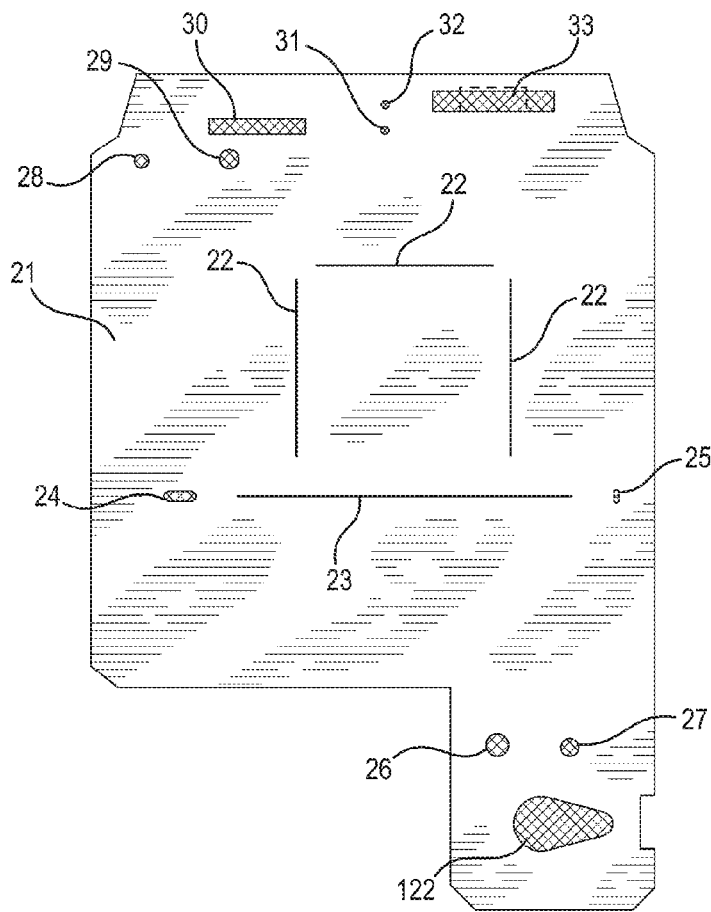
FIG. 3 is a top view of the layout of a tape gasket for an immunosensor cartridge of one embodiment of the invention.
Figure 4:
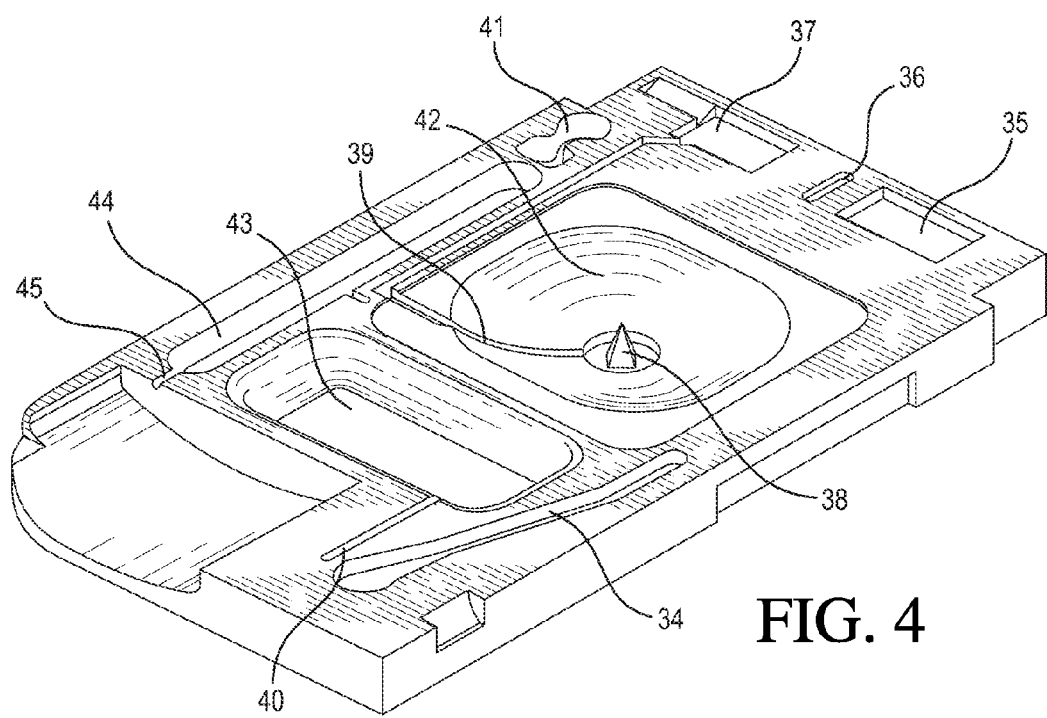
FIG. 4 is an isometric top view of an immunosensor cartridge base of one embodiment of the invention.
Figure 5:
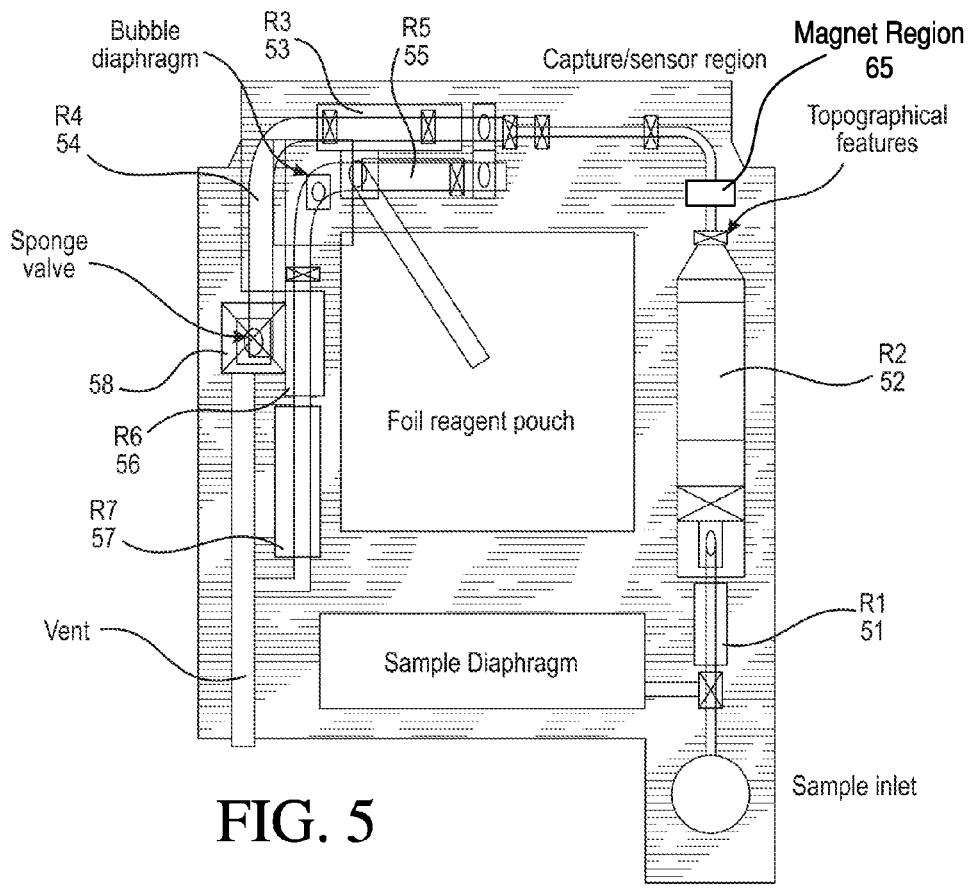
FIG. 5 is a schematic view of the layout of an immunosensor cartridge of one embodiment of the invention.
Figure 6:
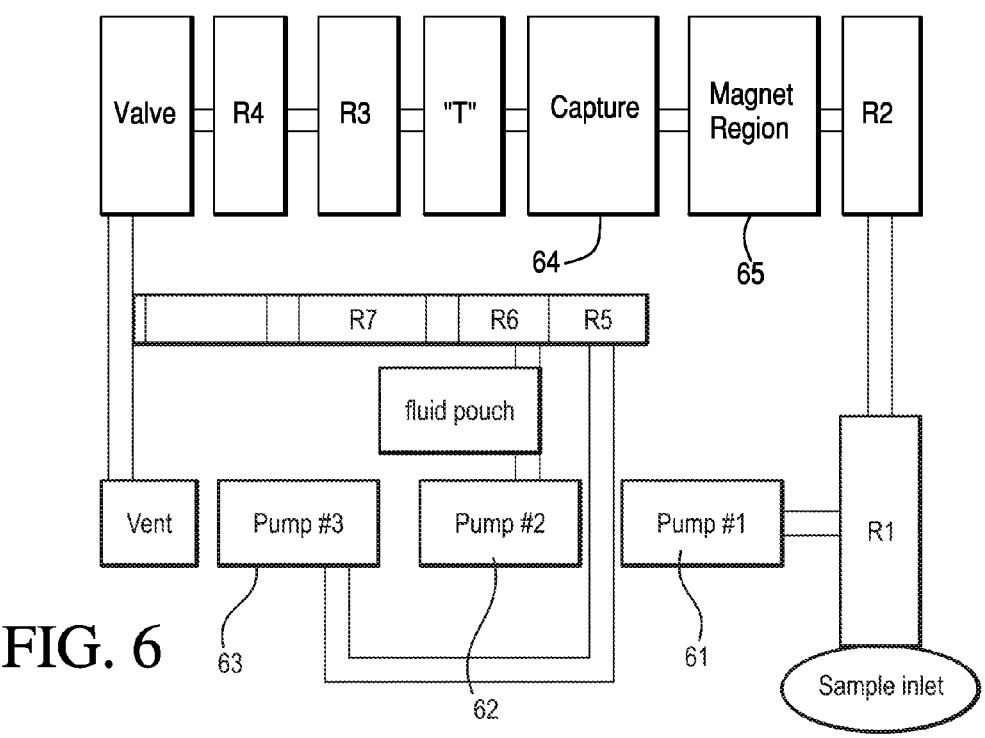
FIG. 6 is a schematic view of the fluid and air paths within an immunosensor cartridge, including sites for amending fluids with dry reagents according to one embodiment of the invention.

In various embodiments, the invention relates to cartridges and methods for processing liquid samples to determine the presence or amount of an analyte in the sample. Preferably the device is a single-use cartridge, e.g., filled with a single sample, used once for the test and then discarded. Referring to the Figures, the cartridge of the present invention comprises a cover, an embodiment of which is shown in FIGS. 1 and 2, a base, an embodiment of which is shown in FIG. 4, a thin-film adhesive gasket disposed between the base and the cover, an embodiment of which is shown in FIG. 3, and a magnet region comprising a permanent magnet or electromagnet, an embodiment of which is shown in FIGS. 5 and 6.

The magnetic field should be generated in a region of the cartridge away from the actual immunosensor. The magnet region can be directly adjacent, e.g., a few millimeters (e.g., 1-25 mm or 1-10 mm) from the immunosensor, or at any other location between the sample entry port and the immunosensor. While it is preferable to magnetically capture the beads upstream of the sensor, capture may optionally be downstream. The important feature is that capture is localized away from the area of the conduit where the immunosensor operates. The magnet can be a permanent fixture in the cartridge or, in another embodiment, may be provided within the instrument (reader) with which the cartridge mates for operation. Thus, in some embodiments, the cartridge may include magnetic sacrificial beads but no magnetic field generating element.

Figure 1:
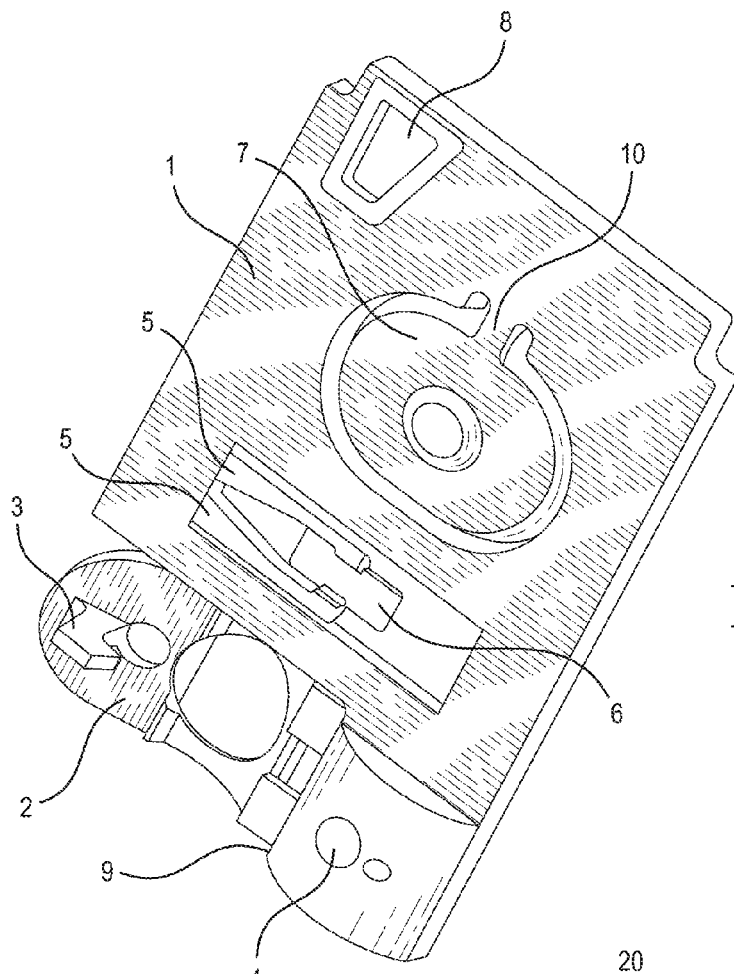
FIG. 1 is an isometric top view of an immunosensor cartridge cover of one embodiment of the invention.

Referring to FIG. 1, the cover 1 is made of a rigid material, preferably plastic, and is capable of repetitive deformation at flexible hinge regions 5, 9, 10 without cracking. The cover comprises a lid 2, attached to the main body of the cover by a flexible hinge 9. In operation, after introduction of a sample into the sample holding chamber 34, the lid can be secured over the entrance to the sample entry port 4, preventing sample leakage, and the lid is held in place by hook 3. The cover further comprises two paddles 6, 7, that are moveable relative to the body of the cover, and which are attached to it by flexible hinge regions 5, 10. When operated upon by a pump means, paddle 6 exerts a force upon an air bladder comprised of cavity 43, which is covered by thin-film gasket 21, to displace fluids within conduits of the cartridge. When operated by a second pump means, paddle 7 exerts a force upon the gasket 21, which can deform because of slits 22 cut therein. The cartridge is adapted for insertion into a reading apparatus, and therefore has a plurality of mechanical and electrical connections for this purpose. In other embodiments of the invention, manual operation of the cartridge is possible.

Upon insertion of the cartridge into a reading apparatus, the gasket transmits pressure onto a fluid-containing foil pack filled with approximately 130 μL of analysis/wash solution ("fluid") located in cavity 42, rupturing the package upon spike 38, and expelling fluid into conduit 39, which is connected via a short transecting conduit in the base to the sensor conduit. The analysis fluid fills the front of the analysis conduit first pushing fluid onto a small opening in the tape gasket that acts as a capillary stop. Other motions of the analyzer mechanism applied to the cartridge are used to inject one or more segments, e.g., air segments, into the analysis fluid at controlled positions within the analysis conduit. These segments are used to help wash the sensor surface and the surrounding conduit with a minimum of fluid.

In certain embodiments of the invention, the cover further comprises a hole covered by a thin pliable film 8. In operation, pressure exerted upon the film expels one or more air segments into a conduit 20 through a small hole 28 in the gasket.

Referring to FIG. 2, the lower surface of the base further comprises second conduit 11, and first conduit 15. Second conduit 11 includes a constriction 12, which controls fluid flow by providing resistance to the flow of a fluid. Optional coatings 13, 14 provide hydrophobic surfaces, which together with gasket holes 31, 32, control fluid flow between second and first conduits 11, 15. A recess 17 in the base provides a pathway for air in conduit 34 to pass to conduit 34 through hole 27 in the gasket.

Referring to FIG. 3, thin-film gasket 21 comprises various holes and slits to facilitate transfer of fluid between conduits within the base and the cover and to allow the gasket to deform under pressure where necessary. Thus, hole 24 permits fluid to flow from conduit 11 into waste chamber 44; hole 25 comprises a capillary stop between conduits 34 and 15; hole 26 permits air to flow between recess 18 and conduit 40; hole 27 provides for air movement between recess 17 and conduit 34; and hole 28 permits fluid to flow from conduit 19 to waste chamber 44 via optional closeable valve 41. Holes 30 and 33 permit the plurality of electrodes that are housed within cutaways 35 and 37, respectively, to contact fluid within conduit 15. In a specific embodiment, cutaway 37 houses a ground electrode, and/or a counter-reference electrode, and cutaway 35 houses at least one analyte sensor and, optionally, a conductimetric sensor. As shown in FIG. 3, the tape 21 is slit at 22 to allow the tape enclosed by the three cuts 22 to deform when the instrument applies a downward force to rupture the calibrant pouch within element 42 on the barb 38. The tape is also cut at 23 and this allows the tape to flex downwards into element 43 when the instrument provides a downward force, expelling air from chamber 43 and moving the sample fluid through conduit 15 towards the sensors. Element 29 in FIG. 3 acts as an opening in the tape connecting a region in the cover FIG. 2 with the base FIG. 4.

As shown in FIG. 4, conduit 34 is the sample holding chamber that connects the sample entry port 4 to first conduit 11 in the assembled cartridge. Cutaway 35 houses the analyte sensor or sensors, or an analyte responsive surface, together with an optional conductimetric sensor or sensors. Cutaway 37 houses a ground electrode if needed as a return current path for an electrochemical sensor, and may also house an optional conductimetric sensor. Cutaway 36 provides a fluid path between gasket holes 31 and 32 so that fluid can pass between the first and second conduits. Recess 42 houses a fluid-containing package, e.g., a rupturable pouch, in the assembled cartridge that is pierced by spike 38 because of pressure exerted upon paddle 7 upon insertion into a reading apparatus. Fluid from the pierced package flows into the second conduit at 39. An air bladder is comprised of recess 43, which is sealed on its upper surface by gasket 21. The air bladder is one embodiment of a pump means, and is actuated by pressure applied to paddle 6 which displaces air in conduit 40 and thereby displaces the sample from sample chamber 34 into first conduit 15.

In certain embodiments of the cartridge, a means for metering a sample segment is provided in the base plastic part. The sample segment size is controlled by the size of the compartment in the base and the position of the capillary stop and air pipe holes in the tape gasket. This volume can be readily varied from 0.001 to 1000 μL, e.g., 1 to 500 μL and 2 to 200

μL. Additional expansion of this range of sample sizes is possible within the context of the present invention.

In some embodiments, the fluid is pushed through a pre-analytical conduit 11 that can be used to amend a reagent (e.g., magnetic sacrificial beads, non-magnetic sacrificial beads, soluble molecules, IgM or fragments thereof, or a combination thereof) into the sample prior to its presentation at the sensor conduit 19. Alternatively, the amending reagent may be located in portion 15, beyond portion 16. Pushing the sample through the pre-analytical conduit also serves to introduce tension into the diaphragm pump paddle 7, which improves its responsiveness for actuation of fluid displacement. The system in which the cartridge operates generally allows the sample to remain in contact with the reagent for a predetermined period, e.g., from 1 to 30 minutes.

The location at which air enters the sample holding chamber (gasket hole 27) from the bladder, and the capillary stop 25, together define a predetermined volume of the sample holding chamber. An amount of the sample corresponding to this volume is displaced into the first conduit when paddle 6 is depressed. This arrangement is one possible embodiment of a metering means for delivering a metered amount of an unmetered sample into the conduits of the cartridge.

According to certain embodiments of the invention, metering is advantageous in some assays if quantification of the analyte is required. As shown in FIG. 4, a waste chamber 44 is provided for sample and/or fluid that is expelled from the conduit, to prevent contamination of the outside surfaces of the cartridge. A vent 45 connecting the waste chamber to the external atmosphere is also provided. One desirable feature of the cartridge of the present invention is that once a biological sample is loaded, analysis can be completed and the cartridge discarded without the operator or others contacting the sample.

FIG. 5 is a schematic diagram a cartridge and its components according to one embodiment of the invention, wherein 51-57 and 65 are portions of the conduits and sample chamber that can optionally be coated with dry reagents to amend a sample or fluid. The biological sample or fluid is passed at least once over the dry reagent to dissolve it. Reagents used to amend the sample may include one or more of the following: the magnetic sacrificial beads of the present invention opsonized with respect to leukocytes, non-magnetic sacrificial beads, antibody-enzyme conjugates (signal antibodies), one or more leukocidal reagents, IgM and/or fragments thereof, IgG and/or fragments thereof, and/or other blocking agents that prevent either specific or non-specific binding reactions among assay compounds. In one embodiment, the reagent includes both magnetic sacrificial beads and non-magnetic sacrificial beds. A surface coating that is not soluble but helps prevent non-specific adsorption of assay components to the inner surfaces of the cartridges can also be utilized in certain embodiments.

As shown in FIGS. 5 and 6, the device includes a magnet region 65, which includes a magnet for retaining the magnetic sacrificial beads and any associated bound leukocytes substantially out of contact from the immunosensor, e.g., upstream of the immunosensor. The magnet region 65 may include a permanent magnet or an electromagnet integrated into the cartridge, e.g., above or below the surface of magnet region 65. In some embodiments, the magnet is positioned in the instrument adjacent to a specified zone of the conduit. In other embodiments, the magnet is embedded into the cartridge body. In a preferred embodiment shown in FIG. 5, the magnet is placed into the cartridge body in the region between the sample holding chamber and the sensing area.

In specific embodiments and as shown in FIG. 5, a closeable valve is provided between the first conduit and the waste chamber. In one embodiment, this valve, 58, is comprised of a dried sponge material that is coated with an impermeable substance. In operation, contacting the sponge material with the sample or a fluid results in swelling of the sponge to fill the cavity 41 (FIG. 4), thereby substantially blocking further flow of liquid into the waste chamber 44 (FIG. 4). The wetted valve also blocks the flow of air between the first conduit and the waste chamber, which permits the first pump means connected to the sample chamber to displace fluid within the second conduit, and to displace fluid from the second conduit into the first conduit.

FIG. 6 illustrates the schematic layout of an immunosensor cartridge of one embodiment of the invention, in which there are provided three pumps, 61-63. While these pumps have been described in terms of specific embodiments, it will be readily understood that any pumping device capable of performing the respective functions of pumps 61-63 may be used within the present invention. Thus, pump 1, 61, should be capable of displacing the sample from the sample holding chamber into the first conduit; pump 2, 62, should be capable of displacing fluid within the second conduit; and pump 3, 63, should be capable of inserting at least one segment into the second conduit. Other types of pumps that are envisaged in the present application include, but are not limited to, an air sac contacting a pneumatic means whereby pressure is applied to the air sac, a flexible diaphragm, a piston and cylinder, an electrodynamic pump, and a sonic pump. With reference to pump 3, 63, the term "pump" includes all devices and methods by which one or more segments are inserted into the second conduit, such as, for example, a pneumatic means for displacing air from an air sac, a dry chemical that produces a gas when dissolved, or a plurality of electrolysis electrodes operably connected to a current source. In a specific embodiment, the segment is produced using a mechanical segment generating diaphragm that may have more than one air bladder or chamber. As shown, well 8 has a single opening which connects the inner diaphragm pump and the fluid filled conduit into which a segment is to be injected 20. The diaphragm can be segmented to produce multiple segments, each injected in a specific location within a fluid filled conduit. In FIG. 6, element 65 indicates the magnet region, and element 64 indicates the region where the immunosensor performs the capture reaction to form a sandwich comprising the immobilized antibody, the analyte and the signal antibody.

In alternative embodiments of the invention, an air segment is injected using a passive feature. A well in the base of the cartridge is sealed by the tape gasket. The tape gasket covering the well has two small holes on either end. One hole is open while the other is covered with a filter material that wets upon contact with a fluid. The well is filled with a loose hydrophilic material such as, for example, cellulose fiber filter, paper filter or glass fiber filter. This hydrophilic material draws the liquid into the well in the base via capillary action, displacing the air that was formerly in the well. The air is expelled through the opening in the tape gasket creating a segment whose volume is determined by the volume of the well and the void volume of the loose hydrophilic material. The filter used to cover one of the inlets to the well in the base can be selected to meter the rate at which the fluid fills the well and thereby control the rate at which the segment is injected into the conduit in the cover. This passive feature permits any number of controlled segments to be injected at specific locations within a fluid path and requires a minimum of space.

As described above, the cartridge of the present invention preferably contains a metering means, which permits an unmetered volume of sample to be introduced, from which a metered amount is processed by the cartridge and its associated reading apparatus. Thus, the physician or operator is relieved of manually measuring the volume of the sample prior to measurement thereby saving time, effort, and increasing accuracy and reproducibility. The metering means, in one embodiment, comprises an elongated sample chamber bounded by a capillary stop and having along its length an air entry point. Air pressure exerted at the air entry point drives a metered volume of the sample past the capillary stop. The metered volume is predetermined by the volume of the sample chamber between the air entry point and the capillary stop.

The cartridge may have a closure device for sealing the sample port in an air-tight manner. This closure device is preferably slidable with respect to the body of the cartridge and may provide a shearing action that displaces excess sample located in the region of the port, thereby reliably sealing a portion of the sample in the holding chamber between the entry port and the capillary stop. See, for example, U.S. Pat. No. 7,682,833, the entirety of which is incorporated herein by reference. In one embodiment, the cartridge may be sealed, for example, by slidably moving a sealing element over the surface of the cartridge in a manner that displaces excess fluid sample away from the sample orifice, seals a volume of the fluid sample within the internal fluid sample holding chamber, and inhibits fluid sample from prematurely breaking through the internal capillary stop. The seal obtained by this slidable closure device is preferably irreversible and prevents excess blood from being trapped in the cartridge because the closure device moves in the plane of the orifice through which blood enters the cartridge and provides a shearing action that seals blood below the plane of the entry port, thereby moving excess blood, i.e., blood above the plane of the orifice, away from the entry port and optionally to a waste chamber.

Figure 15:
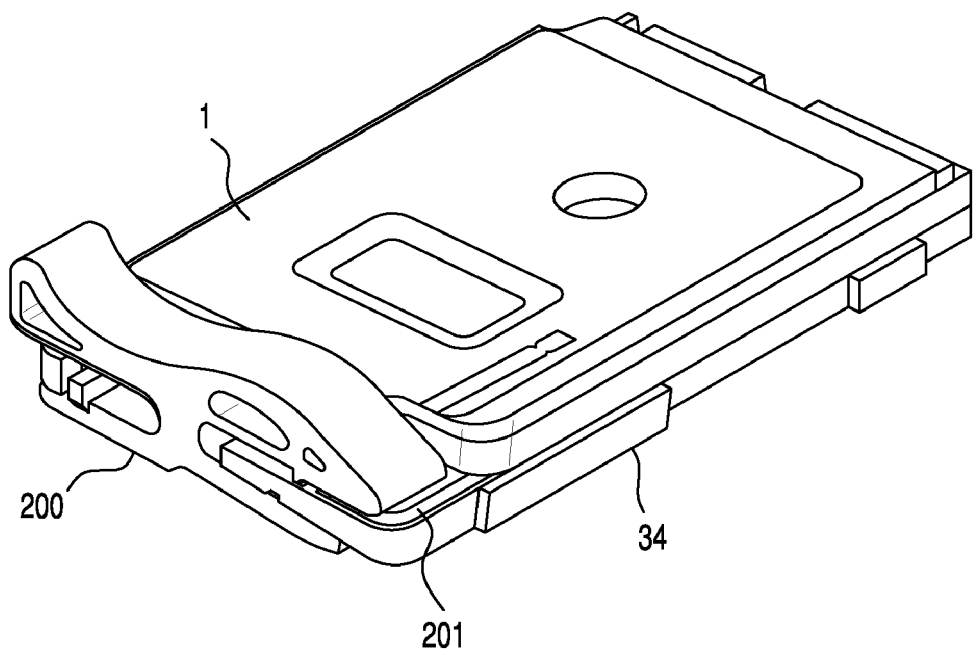
FIG. 15 illustrates the cartridge device of one embodiment of the invention with a slidable sealing element for closing the sample entry port in the closed position.
Figure 16:
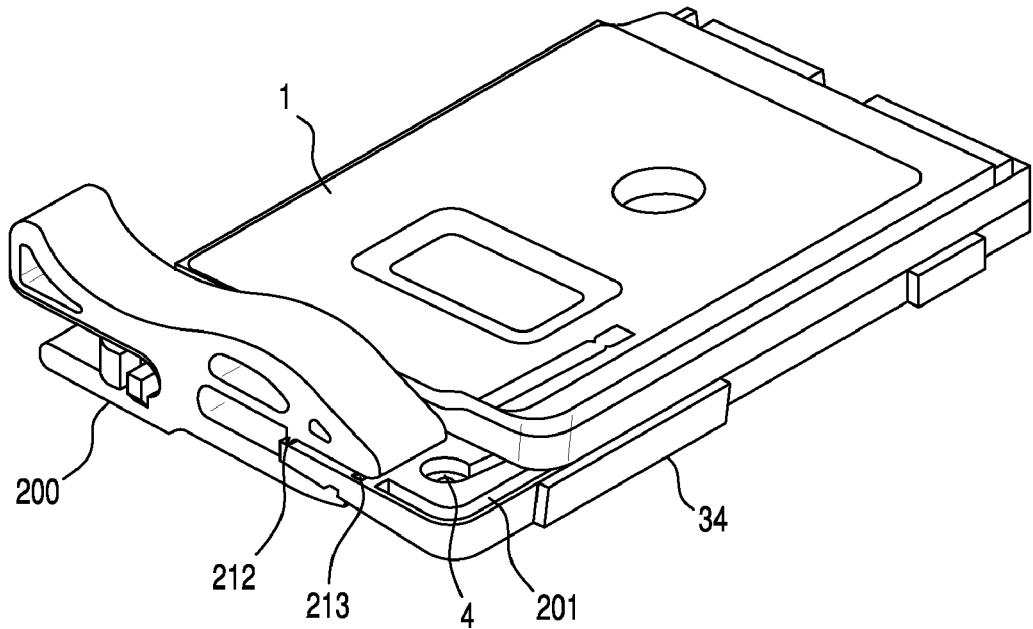
FIG. 16 illustrates the cartridge device of one embodiment of the invention with a slidable sealing element for closing the sample entry port in the open position.

An exemplary closure device of one embodiment of the present invention is shown in FIG. 1 and comprises integrated elements 2, 3, 4 and 9 of cover 1. In this embodiment, closure device 2 rotates about a hinge until hook 3 snaps shut blocking sample entry port 4. An alternative to the closure device comprising integrated elements 2, 3, 4 and 9 of cover 1 in FIG. 1 is shown as a separate slidable element 200 in FIGS. 15 and 16. FIGS. 15 and 16 show a cartridge device comprising a modified version of the cover of FIG. 1 attached to a base similar to the base in FIG. 4 with intervening adhesive layer 21 shown in FIG. 3 along with the separate slidable closure element 200. FIG. 16 shows the closure device 200 in the open position, where the sample entry port 4 can receive a sample, e.g., blood. FIG. 15 shows the closure device 200 in the closed position where it seals the sample entry port in an air-tight manner. In operation, element 200 is manually actuated from the open to the closed position after the sample, e.g., blood, has been added to the entry port and enters the holding chamber 34. In the embodiment shown, any excess blood in the region of the entry port is moved into an overflow chamber 201 or an adjacent retaining region or cavity. This chamber or region may include a fluid-absorbing pad or material to retain the excess sample, e.g., blood.

The sample entry port 4 may be an orifice that is circular, as shown in FIG. 16, or oval and the diameter of the orifice is generally in the range 0.2-5 mm, preferably 1-2 mm, or having a perimeter of 1-15 mm for an oval. The region around the orifice may be selected to be hydrophobic or hydrophilic to control the drop-shape of the applied sample to promote entry into the entry port. One advantage of the closure device shown in FIGS. 15 and 16 is that it prevents the sample from being pushed beyond the capillary stop element 25 at the end of the holding chamber 34. The presence of a small amount of sample, e.g., blood, beyond the capillary stop is not significant for tests that measure bulk concentration of an analyte and thus do not depend on sample volume. However, for immunoassay applications where metering of the sample is generally advantageous, the sealing element improves metering accuracy of the device and assures the assayed segment of sample is appropriately positioned with respect to the immunosensor when the analyzer actuates the sample within the cartridge conduits.

In operation, when the sample, e.g., blood, is added to the cartridge it moves to the capillary stop. Thus, sufficient sample for the assay is present when the region from the capillary stop to the sample entry port, i.e., the holding chamber 34, contains the sample. During the process of filling the holding chamber, some sample may remain above the plane of the orifice of the entry port. When the sealing element is moved from the opened to closed position, any sample that is above the entry port is sheared away without trapping additional sample in the act of closure, thereby ensuring that the sample does not move beyond capillary stop 25. In a preferred embodiment, sealing element 200 is positioned within a few thousandths of an inch above the surface of the tape gasket 21 of FIG. 3. The entry port is sealed by the subsequent lowering of the surface of 200 to the adhesive tape gasket when it engages locking features 212 and 213. As the tape is essentially incompressible and the orifice has a small diameter, any inadvertent pressure applied to the sealing element by the user will not cause the sample to move beyond the capillary stop.

In certain cartridge embodiments where several drops of sample are analyzed, it is desirable that no bubbles form in the holding chamber, as this can affect the assay. Accordingly, a reliable means for introducing more than one drop of sample, e.g., blood, into the holding chamber 34 without entraining bubbles has been developed. In accordance with one embodiment of the invention, the sample entry port is designed to receive multiple drops of sample without successive drops causing trapped bubbles to form in the holding chamber 34 by first treating the holding chamber with a Corona and/or a reagent cocktail.

The use of Corona treatments on disposable medical devices is well known in the art and is an effective way to increase the surface activity of virtually any material, e.g., metallized surfaces, foils, paper, paperboard stock, or plastics such as polyethylene, polypropylene, nylon, vinyl, polyvinyl chloride (PVC), and polyethylene terephthalate (PET). The Corona treatment makes the materials more receptive to inks, coatings, and adhesives. In practice, the material being treated is exposed to an electrical discharge or "corona." Oxygen molecules in the discharge area break into atoms and bond to molecules in the material being treated, resulting in a chemically activated surface. Suitable equipment for Corona treatments is commercially available (e.g., Corotec Corporation, Farmington, Conn., USA). The process variables are well known and include, for example, the amount of power required to treat the material, material speed, width, number of sides to be treated, and responsiveness of a particular material to Corona treatment. The typical Corona treatment installation location is in-line with the printing, coating, or laminating process. Another common installation is directly on a blown film or cast film extruder, because fresh material is relatively more receptive to Corona treatment.

The cartridge of the present invention has the advantage that the sample and a second fluid can contact the sensor array at different times during an assay sequence. The sample and the second fluid also may be independently amended with other reagents or compounds present initially as dry coatings within the respective conduits. Controlled motion of the liquids within the cartridge further permits more than one substance to be amended into each liquid whenever the sample or fluid is moved to a new region of the conduit. In this way, provision is made for multiple amendments to each fluid, greatly extending the complexity of automated assays that can be performed, and therefore enhancing the utility of the present invention.

In some embodiments of the invention, the cartridge is disposable. In a disposable cartridge, the amount of liquid contained is preferably kept small to minimize cost and size. In the present invention, segments within the conduits may also be used to assist in cleaning and rinsing the conduits by passing the air-liquid interface of a segment over the sensor array or other region to be rinsed at least once. It has been found that more efficient rinsing, using less fluid, is achieved by this method compared to continuous rinsing by a larger volume of fluid.

Restrictions within the conduits serve several purposes in the present invention. In one embodiment, a capillary stop located between the sample holding chamber and first conduit is used to facilitate sample metering in the holding chamber by preventing displacement of the sample in the holding chamber until sufficient pressure is applied to overcome the resistance of the capillary stop. In another embodiment, a restriction within the second conduit is used to divert wash fluid along an alternative pathway towards the waste chamber when the fluid reaches the constriction. Small holes in the gasket, together with a hydrophobic coating, are provided to prevent flow from the first conduit to the second conduit until sufficient pressure is applied. Features that control the flow of liquids within and between the conduits of the present invention are herein collectively termed "valves."

One embodiment of the invention provides a single-use cartridge with a sample holding chamber connected to a first conduit that contains an analyte sensor or an array of analyte sensors. A second conduit, partly containing a fluid, is connected to the first conduit and air segments can be introduced into the fluid in the second conduit in order to segment it. Pump means are provided to displace the sample within the first conduit, and this displaces fluid from the second conduit into the first conduit. Thus, the sensor or sensors can be contacted first by a sample and then by a second fluid.

In another embodiment, the cartridge includes a closeable valve located between the first conduit and a waste chamber. This embodiment permits displacement of the fluid from the second conduit into the first conduit using only a single pump means connected to the first conduit. This embodiment further permits efficient washing of the conduits of the cartridge of the present invention, which is an important feature of a small single-use cartridge. In operation, the sample is displaced to contact the sensors, and is then displaced through the closeable valve into the waste chamber. Upon wetting, the closeable valve seals the opening to the waste chamber, providing an airtight seal that allows fluid in the second conduit to be drawn into contact with the sensors using only the pump means connected to the first conduit. In this embodiment, the closeable valve permits the fluid to be displaced in this manner and prevents air from entering the first conduit from the waste chamber.

In another embodiment, both a closeable valve and means for introducing segments into the conduit are provided. This embodiment has many advantages, among which is the ability to reciprocate a segmented fluid over the sensor or array of sensors. Thus a first segment or set of segments is used to rinse a sensor, and then a fresh segment replaces it for taking measurements. Only one pump means (that connected to the first conduit) is required.

II. Signal Generating Reactions

As described above, the non-competitive (sandwich) immunoassay format is the most widely used immunoassay method and is a preferred format in the analysis device, e.g., cartridge, of the present invention. In this embodiment, one antibody (the immobilized antibody) is bound to a solid support or immunosensor, and a second antibody (the signal antibody) is conjugated/bound to a signal-generating reagent such as an enzyme, e.g., alkaline phosphatase.

Figure 17:
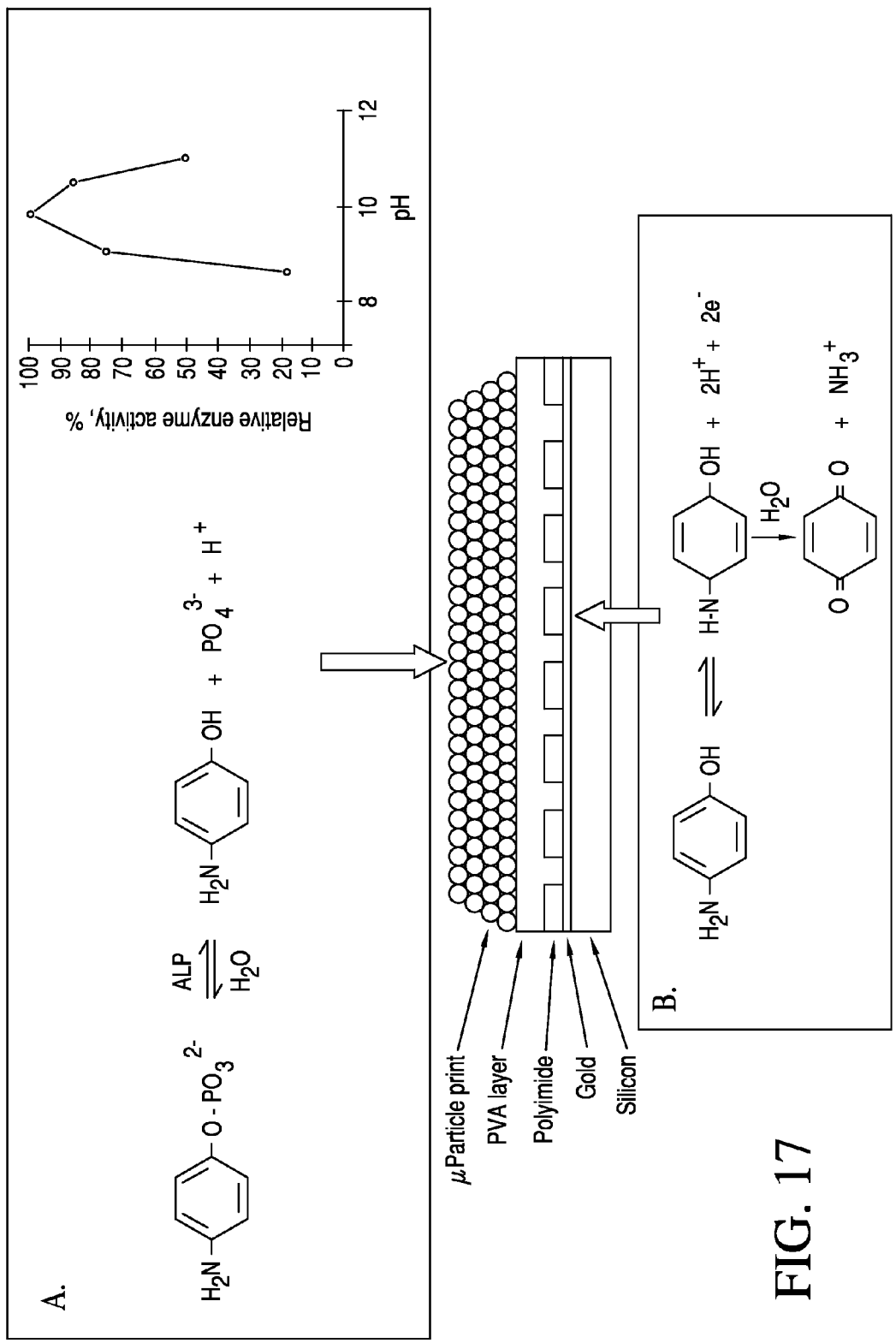
FIG. 17 illustrates the signal generating reactions occurring during the analysis: (a) cleavage of substrate by alkaline phosphatase to generate electroactive p-aminophenol and (b) oxidation of p-aminophenol.

Briefly, FIG. 17 illustrates the signal generating reactions occurring during the analysis with FIG. 17(a) showing the cleavage of substrate by alkaline phosphatase to generate electroactive p-aminophenol and FIG. 17(b) showing oxidation of p-aminophenol. The reaction in FIG. 17(a) occurs in the upper layer of the sensor structure while that in FIG. 17(b) occurs at the gold electrode surface. The inset in FIG. 17(a) illustrates the pH-dependence of the alkaline phosphatase catalyzed hydrolysis. The central illustration depicts the gross features of the immunosensor structure prior to exposure to sample.

The signal-generating reagent (e.g., signal antibody for non-competitive assays or labeled analyte for competitive assays) may be part of a dry reagent coating in the analysis device, as described below, and preferably dissolves into the biological sample before the sample reaches the immunosensor. For non-competitive assays, after washing away the sample and non-specifically bound reagents, the amount of signal-generating reagent (e.g., signal antibody) remaining on the solid support should in principle be proportional to the amount of analyte in the sample. For competitive assays, as discussed above, after washing away the sample and non-specifically bound reagents, the amount of signal-generating reagent (e.g., labeled analyte) remaining on the solid support should in principle be inversely proportional to the amount of analyte in the sample. However, one limitation of these assay configurations is the susceptibility to interference(s) caused by leukocytes present in the sample.

In alternative embodiments, the enzyme conjugated to an antibody or other analyte-binding molecule is urease, and the substrate is urea. Ammonium ions produced by the hydrolysis of urea are detected in this embodiment by the use of an ammonium sensitive electrode. Ammonium-specific electrodes are well-known to those of skill in the art. For example, a suitable microfabricated ammonium ion-selective electrode is disclosed in U.S. Pat. No. 5,200,051, incorporated herein by reference. Other enzymes that react with a substrate to produce an ion are known in the art, as are other ion sensors for use therewith. For example, phosphate produced from an alkaline phosphatase substrate can be detected at a phosphate ion-selective electrode.

III. Magnetic Sacrificial Beads

In various embodiments of the invention, the biological sample, e.g., blood sample, is amended with "sacrificial" or "decoy" magnetic beads specifically opsonized with respect to leukocytes. In preferred embodiments, the magnetic sacrificial beads are homogeneously mixed with the sample. In other embodiments, the magnetic sacrificial beads may be less homogeneously mixed with the sample, however the intent is to capture as many leukocytes as possible. Utilization of the magnetic sacrificial beads permits substantial removal of the leukocytes from the biological sample before the sample reaches the immunosensor.

For example, in one embodiment, similar to the sandwich assay process described above, the magnetic sacrificial beads are mixed with the biological sample, e.g. blood, in the holding chamber of the cartridge, and optionally also with the enzyme labeled second antibody. The sample is then oscillated, optionally in the holding chamber, to promote mixing, during which the leukocytes become associated with the opsonized magnetic beads. Mixing may occur for a predetermined period, e.g., for the first 1 to 5 minutes of the assay cycle. In the next step of the assay, the sample is moved through the conduit towards the immunosensor. As previously described, the immunosensor has the capture antibody for the analyte. At a region of the conduit proximate to the holding chamber with respect to the immunosensor, the magnetic beads enter a magnet region where an applied magnetic field is sufficient to retain a majority, preferably substantially all, e.g., at least 50 wt. %, at least 75 wt. %, at least 85 wt. %, or at least 90 wt. %, of the sacrificial beads out of the fluid and effectively affix them to the wall of the magnet region (typically a conduit). Essentially, as the pump in the cartridge is activated and moves the sample forward thorough the conduit, the magnetic sacrificial beads are able to resist the pneumatic force and remain in the magnet region due the magnetic field that is applied by the magnet. The remaining portion of the sample continues to the immunosensor region. After sandwich formation on the immunosensor (for heterogeneous non-competitive embodiments), the blood sample preferably is washed into a waste chamber and a reagent that reacts with the label, e.g., ALP, is added.

In some embodiments, the magnetic field may be generated by a permanent magnet or electromagnet in the instrument adjacent to the specified zone of the conduit. In other embodiments, a magnet is embedded into the cartridge body. The magnet utilized in the present invention can be of any shape, size and magnetic material known in the art. In a preferred embodiment shown in FIG. 5, the magnet is positioned in the cartridge body in the magnet region 65 between the sample holding chamber and the sensing area. In all such embodiments, the interaction between the magnet and the magnetic sacrificial beads prevents a substantial portion of the leukocytes in the sample from reaching the immunosensor region of the conduit. In this context, the term "substantial" or "substantially", means an amount greater than 50 wt. %.

The magnetic sacrificial beads may be comprised of any material known in the art that is susceptive to a magnet, e.g., permanent magnet or electromagnet, utilized in or in concert with the device of the present invention. In some embodiments of the invention, the sacrificial beads include a magnetic core, which preferably is completely or partially coated with a coating material. The magnetic core may comprise one or more of Fe, Co, Mn, Ni, metals comprising one or more of these elements, ordered alloys of these elements, crystals comprised of these elements, magnetic oxide structures, such as ferrites, and combinations thereof. In other embodiments, the magnetic core may be comprised of magnetite ($Fe_3O_4$), maghemite ($\gamma\text{-}Fe_2O_3$), or divalent metal-ferrites provided by the formula $Me_{1-x}OFe_3+xO_3$ where Me is for example Cu, Fe, Ni, Co, Mn, Mg, or Zn or combinations of these materials, and where x ranges from 0.01 to 99.

Suitable materials for the coating include synthetic and biological polymers, copolymers and polymer blends, and inorganic materials. Polymer materials may include various combinations of polymers of acrylates, siloxanes, styrenes, acetates, alkylene glycols, alkylenes, alkylene oxides, parylenes, lactic acid, and glycolic acid. Inorganic coating materials may include any combination of a metal, a metal alloy, and a ceramic. Examples of ceramic materials may include hydroxyapatite, silicon carbide, carboxylate, sulfonate, phosphate, ferrite, phosphonate, and oxides of Group IV elements of the Periodic Table of Elements. In preferred embodiments of the invention, the magnetic beads are comprised of magnetite ($Fe_3O_4$) and coated with a styrene-acrylic acid copolymer to provide a surface decorated with carboxyl groups.

In other embodiments of the invention, the magnetic sacrificial beads comprise non-magnetic substrate beads formed, for example, of a material selected from the group consisting of polystyrene, polyacrylic acid and dextran, upon which a magnetic coating is placed.

In principal, any correctly-sized magnetic bead capable of being opsonized for leukocytes may be utilized in the present invention taking into account the dispersability requirements for the magnetic sacrificial beads. In some exemplary embodiments, the average particle size of the magnetic sacrificial beads may range from 0.01 to 20 µm, e.g., from 0.1 to 10 µm, from 1 to 5 µm, or from 3 to 5 µm. As used herein, the term "average particle size" refers to the average longest dimension of the particles, for example the diameter for spherical particles, as determined by methods well-known in the art. The particle size distribution of the magnetic sacrificial beads preferably is unimodal, although polymodal distributions may also be used in accordance with the present invention.

While use of a spherical magnetic bead is preferred, in other embodiments, other bead shapes and structures, e.g., ovals, sub-spherical, cylindrical and other irregular shaped particles, are within the meaning of the term "beads" as well as the term "microparticle" as used and defined herein.

The magnetic beads may be coated with a variety of surface coating materials, so that the surface coating is opsonized or opsonizable upon exposure to a sample to be assayed. In some embodiments, the magnetic sacrificial beads are coated with non-human IgG (IgG class immunoglobulins) or fragments thereof isolated from animal species. As used herein, the term "fragment" refers to any epitope-bearing fragment derived from the specified molecule. Thus, an IgG fragment may comprise, for example, epitope bearing F(ab')2 or Fab fragments or an Fc fragment. In addition, the phrase "IgG or fragments thereof" is meant to include IgG alone, IgG fragments alone (i.e., one or more of F(ab')2 fragments, Fab fragments and/or Fc fragments of IgG), or a combination of IgG and IgG fragments. In preferred embodiments of the invention, goat or sheep IgG coated particles are employed, although other IgG sources may be employed such as, for example, mouse or rabbit IgG.

In addition to or instead of coating the magnetic sacrificial beads using whole IgG molecules, where the individual monomers are formed from an Fc region attached to a F(ab')2 region, which in turn comprises two Fab regions, it is also possible to use fragments of IgG as defined above. IgG fragmentation can be achieved variously using combinations of disulphide bond reduction (—S—S— to —SH HS—) and enzymatic pepsin or papain digestion, to create some combination of F(ab')2 fragments, Fab fragments, and/or Fc fragments. These fragments can be separated for use separately by chromatography, or used in combination. For example, where the blocking site is on the Fc fragment, this can be used instead of the whole IgG molecule. The same applies to the Fab fragment and the F(ab')2 fragment.

Relatively smaller sacrificial beads, e.g., those having an average particle size less than 0.2 µm, coated with IgG may be used, but preferably the average particle size of the IgG-coated magnetic sacrificial beads is in the range of 3-5 µm.

Those skilled in the art will recognize that the magnetic beads of the present invention may be added to the biological sample prior to introduction into the cartridge, such as, for example, as an integral part of a blood collection device or as a standard manual addition step. However, for the convenience of the user and to assure a quality assay, the magnetic beads are preferably included within the test device.

In one embodiment, the magnetic sacrificial beads are incorporated into a dry reagent coating. In some embodiments, at least a portion of the cartridge housing may be coated with a dry reagent which can comprise non-human IgG-coated magnetic sacrificial beads. The important feature is that the dry reagent is capable of dissolving into the sample and engaging leukocytes in binding. This is generally sufficient to sequester potentially interfering leukocytes in the sample.

In certain embodiments, the magnetic sacrificial beads are incorporated into the same dry reagent coating that contains the signal-generating reagent (e.g., signal antibody for non-competitive assays or labeled analyte for competitive assays). Thus, in one embodiment of the invention, the analysis device includes a dry reagent coating that comprises either or both: (a) a component suitable for ameliorating the effect of leukocytes, e.g., magnetic sacrificial beads coated with IgG or fragments thereof, and/or (b) a signal-generating reagent such as a signal antibody or a labeled analyte.

The present invention is also directed to methods of performing an immunoassay for a target analyte in a biological sample. In one embodiment, the method comprises performing an analyte sandwich immunoassay comprising introducing a blood sample containing leukocytes into a holding chamber in a test cartridge, wherein a portion of the holding chamber is coated with magnetic sacrificial beads opsonized to leukocytes; contacting the blood sample with the magnetic sacrificial beads under conditions sufficient to bind at least a portion of the leukocytes in the biological sample to the magnetic sacrificial beads; moving the blood sample into a conduit; applying a magnetic field localized to at least a portion of the conduit to attract and retain the magnetic sacrificial beads on at least a portion of the wall of the conduit thereby substantially preventing the magnetic sacrificial beads from coming into contact with an immunosensor; contacting the blood sample with the immunosensor to form a sandwich comprising an immobilized capture antibody, a sample analyte and a labeled signal antibody; washing the blood sample from the immunosensor; and contacting the immunosensor with a reagent capable of reacting with said labeled signal antibody to produce a signal at the immunosensor related to the presence of the sample analyte in the blood sample.

This same general approach is also suitable for competitive immunoassays. In substantially the same cartridge format described above for a sandwich assay, the leukocytes are substantially removed from the sample by magnetic means, prior to the competitive binding of analyte and labeled analyte that occurs at the immunosensor (for heterogeneous competitive assays) or on mobile particles (for homogeneous competitive assays).

The specifics of performing a heterogeneous competitive analyte immunoassay include the steps of introducing a blood sample containing leukocytes into a holding chamber in a test cartridge, wherein a portion of the holding chamber is coated with magnetic sacrificial beads opsonized to leukocytes; contacting the blood sample with the magnetic sacrificial beads under conditions sufficient to bind at least a portion of the leukocytes in the biological sample to the magnetic sacrificial beads; moving the blood sample into a conduit; applying a magnetic field localized to at least a portion of the conduit to attract and retain the magnetic sacrificial beads on at least a portion of the wall of the conduit thereby substantially preventing the magnetic sacrificial beads from coming into contact with an immunosensor; contacting the blood sample with an immunosensor to form a competitive ratio of bound sample analyte to bound labeled analyte; washing the blood sample from the immunosensor; and contacting the immunosensor with a reagent capable of reacting with the labeled analyte to produce a signal at the immunosensor that is inversely related to the presence of the sample analyte in the blood sample.

IV. Additives

In some embodiments of the invention, additives may be included in the cartridge or used in conjunction with the assay. In certain embodiments, an anticoagulant can be added. For example, in some embodiments, heparin is added to improve performance in cases where the sample was not collected in a heparinized tube or was not properly mixed in a heparinized tube. A sufficient amount of heparin is added so that fresh unheparinized blood will remain uncoagulated during the assay cycle of the cartridge, typically in the range of 2 to 20 minutes. In other embodiments, goat and mouse IgG can be added to combat heterophile antibody problems known in the immunoassay art. In still other embodiments, one or more of proclin, DEAE-dextran, tris buffer, and lactitol can be added as reagent stabilizers. In further embodiments, a surfactant such as for example polysorbate 20, also known as Tween® 20, can be added to reduce binding of proteins to plastic, which is a preferred material for the cartridge. The addition of a surfactant also facilitates the even coating of reagents on plastic surfaces and minimizes the crystallization of sugars (e.g., lactitol). In other embodiments of the invention, a antibacterial agent or biocide (e.g., sodium azide) may be added to inhibit bacterial growth.

V. Preparation of Print Cocktail and Printing

Magnetic beads/microparticles are available commercially in a variety of forms. The magnetic core may be either a magnetic or superparamagnetic material. Typically the core is coated with a polymeric, e.g., polystyrene, polyacrylic acid, or biopolymer, e.g., a starch or similar carbohydrate. Commercial sources for magnetic bead preparations include Invitrogen™, Ademtech (Pessac, FR) and Chemicell GmbH (Berlin). Many of these products incorporate surface functionalization that can be employed to immobilize antibodies, e.g., IgG, on the microparticles, e.g. -carboxyl, -amino or streptavidin modified magnetic beads. Magnetic bead preparations can be deposited in suitable regions of a device as a suspension in, for example, a mixture of lactitol and DEAE-dextran such as that supplied by Advanced Enzyme Technologies (Pontypool, UK). Evaporation of the solvent, usually water, yields a glassy deposit in which the beads are immobilized. The lactitol/DEAE-dextran allows the microparticles to be regionalized within the device in a mechanically and biochemically stable state which dissolves upon contact with a sample.

In a preferred embodiment, the base print cocktail is prepared as follows for a 1 liter (L) batch: protein stabilization solution (PSS, AET Ltd., 50% solids, 100.0 g) is added to 200-250 mL of an aqueous solution of sodium chloride (8.00 g) and sodium azide (0.500 g) and the resulting solution is transferred to a 1 L volumetric flask. A solution of murine IgG is prepared by adding murine IgG (0.9 g) to 75 mL of deionized water and stirred for 15-60 minutes until dissolution is complete. An equally concentrated solution of caprine IgG is prepared in an identical manner and both solutions are filtered through a 1.2 µM filter. Murine IgM is acquired as a liquid from a supplier (e.g., Sigma-Aldrich). The protein concentrations of each of the three immunoglobulin (Ig) stock solutions are measured spectrophotometrically at 280 nm. The masses of these Ig solutions required to provide murine IgG (0.75 g), caprine IgG (0.75 g), and murine IgM (25 mg) are calculated and these amounts are added to the printing solution. A solution of diethylaminoethyl-dextran (DEAE-dextran) is prepared by adding DEAE-dextran (2.5 g) to 50-100 mL of deionized water and stirring for 30 minutes. The DEAE-dextran solution is added to the printing solution. To this is added sodium heparin (10,000 IU/mL, 3.00 mL), Tween® 20 (3.00 g) and a 5% (w/v) aqueous solution of rhodamine (200 µL). The resulting solution is diluted to 1.000 L with deionized water and stored in a freezer or refrigerator until use. The IgG-coated magnetic beads for leukocyte interference reduction or elimination (optionally in combination with IgG-coated non-magnetic beads) can be added before this final dilution or just prior to deposition into a test device, e.g., a cartridge of any of the types shown in FIGS. 1-6.

In various embodiments of the invention, printing of print cocktails and similar fluids to form a dry reagent coating on the cartridge component is preferably automated and based on a microdispensing system, including a camera and computer system to align components, as disclosed in U.S. Pat. No. 5,554,339 to Cozzette et al. (the "'339 patent"), which is incorporated herein by reference in its entirety. In the '339 Patent, the wafer chuck is replaced by a track for feeding the plastic cartridge bases to the dispensing head. The track presents the bases to the head in a predetermined orientation to ensure consistent positional dispensing.

VI. Collection and Analysis

According to various embodiments of the invention, the blood sample is obtained using a sample collection device such as a capillary, Vacutainer® or syringe. In one embodiment, the magnetic sacrificial beads may be incorporated in the sample collection device, e.g., capillary, Vacutainer® or syringe. In some embodiments, the magnetic sacrificial beads coating may be formed on an interior wall of the collection device.

VII. Immunosensor Embodiments and Methods Related Thereto

While the present invention is broadly applicable to immunoassay systems, it is best understood in the context of the i-STAT® immunoassay system (Abbott Point of Care Inc., Princeton, N.J., USA), as described in the jointly-owned pending and issued patents cited above. See also U.S. Patent Application No. 61/288,189, entitled "Foldable Cartridge Housings for Sample Analysis," filed Dec. 18, 2009, the entirety of which is incorporated herein by reference.

In various embodiments, the system employs an immuno-reference sensor (See, e.g., U.S. Pat. Appl. Pub. 2006/0160164 to Miller et al., referenced above and incorporated herein by reference in its entirety) for purposes of assessing the degree of non-specific binding (NSB) occurring during an assay. In some instances, NSB may arise due to inadequate washing or due to the presence of interferences. The net signal from the assay is comprised of the specific signal arising from the analyte immunosensor corrected by subtracting the non-specific signal arising from the immuno-reference sensor. The amount of signal at the immuno-reference sensor is subject to limits defined by a quality control algorithm. The immunosensor is preferably directed to detect a cardiovascular marker, e.g., analytes such as TnI, TnT, CKMB, myoglobin, BNP, NT-proBNP, and proBNP.

Embodiments of the present invention improve the resistance of the i-STAT® immunoassay format to interference caused by leukocytes. In these embodiments, a biological sample is amended with the magnetic sacrificial beads of the present invention to provide reduced or eliminated leukocyte interference. Such embodiments are equally applicable to the standard ELISA format, where cells are present in the analysis medium.

While traditional sandwich assays may yield erroneous results for biological samples having a high leukocyte level, prior i-STAT® system assays did not report inaccurate results for these samples, as the system includes an algorithm that detects spurious signals, alerts the user with an error code, and suppresses the result from being displayed. This is one embodiment of a quality system for reliable point-of-care testing in which the quality and integrity of the analytical system is maintained.

Figure 9:
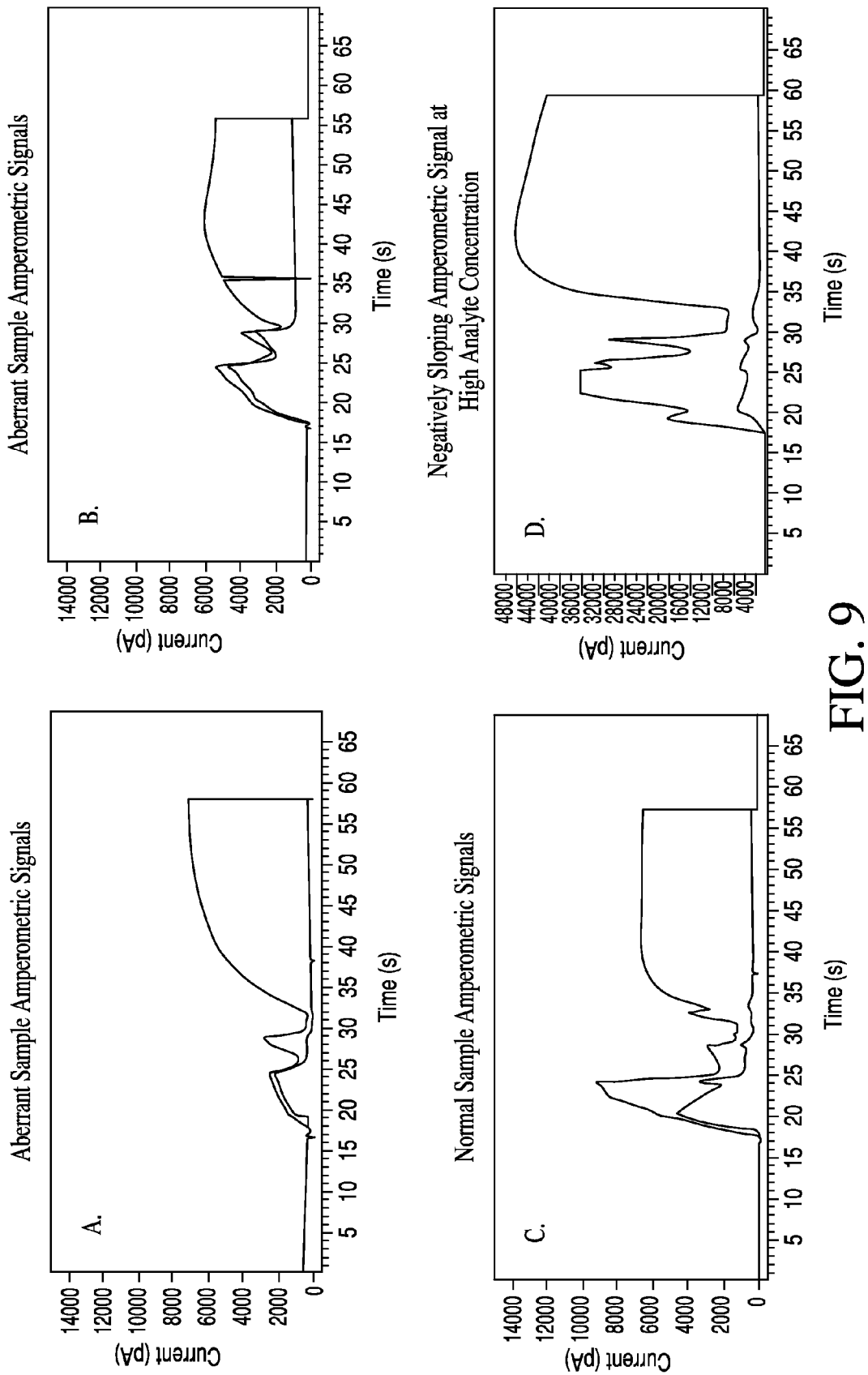
FIG. 9($a$) shows an unexpected waveform for a brain natriuretic peptide (BNP) cartridge with a positively sloping output signal.

With regard to the subject matter of the present invention, it was discovered that certain immunoassay test cartridges, notably brain natriuretic peptide (BNP) cartridges, exhibited unexpected positively and negatively sloping waveforms arising from a previously unknown interference mechanism. See, for example, FIG. 9(a) and (b), respectively. This led to a hypothesis concerning the mechanism of the interference based on experiments on the effect of pulsing the electrode to positive potentials during the wash step. As shown in FIGS. 9(c) and (d), the normal immunosensor response, expected on a theoretical basis, has a near-zero slope at low analyte concentrations, and negative slopes are expected only at high analyte concentrations where the measurement can become substrate-limited rather than enzyme limited.

There are several potential mechanisms causing dynamic (non-steady state) amperometric signals. Dynamic electrode activity (changing effective electrode area) is unlikely because the electrode is sequestered from formed elements owing to the presence of immobilized assay beads (microparticles) on a polyvinyl alcohol (PVA) layer, neither of which exhibit this effect in plasma samples. Dynamic layer thickness, e.g., swelling or shrinking of the components above, depending on fluid contact, is unlikely as there is no driving force for such a phenomenon that would elicit both positive and negative slopes. Dynamic coverage of the enzyme (e.g., ALP, changing surface concentration of enzyme) is ruled out because in the thin-layer format, diffusion of enzyme (e.g., ALP) from the sensor over the time-scale of the measurement is not possible. Dynamic transport of the enzyme substrate, e.g., para-aminophenol phosphate (p-APP), to the electrode surface is unlikely given the size of the molecule, which is relatively small and has a relatively facile diffusion (D≈5× $10^{-6}$ cm$^2$/s). Thus, by the process of elimination and without wishing to be bound by theory, dynamic ALP activity was considered the most likely cause of dynamic sensor signals and further investigation was made to assess the mechanism. The hydrolysis of p-APP by ALP is pH-dependent with an optimum near pH 10. In some embodiments, in the cartridge, a working pH of 9.2 is used as this slightly lower pH value ensures stability of immunocomplexes. In addition, the oxidation of para-aminophenol (p-AP) at the electrode is pH dependent and is expected to shift by about +59 mV per decade decrease in pH, i.e., at lower pH the reaction must be driven harder, i.e., an increased applied potential is required.

In embodiments where the print layer was to become less permeable due to interaction with the interfering components to the extent that sample fluid (pH 7.4) within the sensor structure could not be fully replaced with analysis fluid (pH 9.2) during the wash step, this results in suboptimal detection step pH, particularly for the electrode reaction which occurs at a region farthest from the point of entry of the analysis fluid. This impaired fluid replacement creates a pH gradient that undergoes relaxation with time. As the relative rates of the enzyme and electrode reactions change, so will the observed signal. This technical evaluation has the considerable advantage that it offers an explanation for both positive and negatively sloping signals. See, e.g., FIGS. 9(a) and (b).

Figure 10:
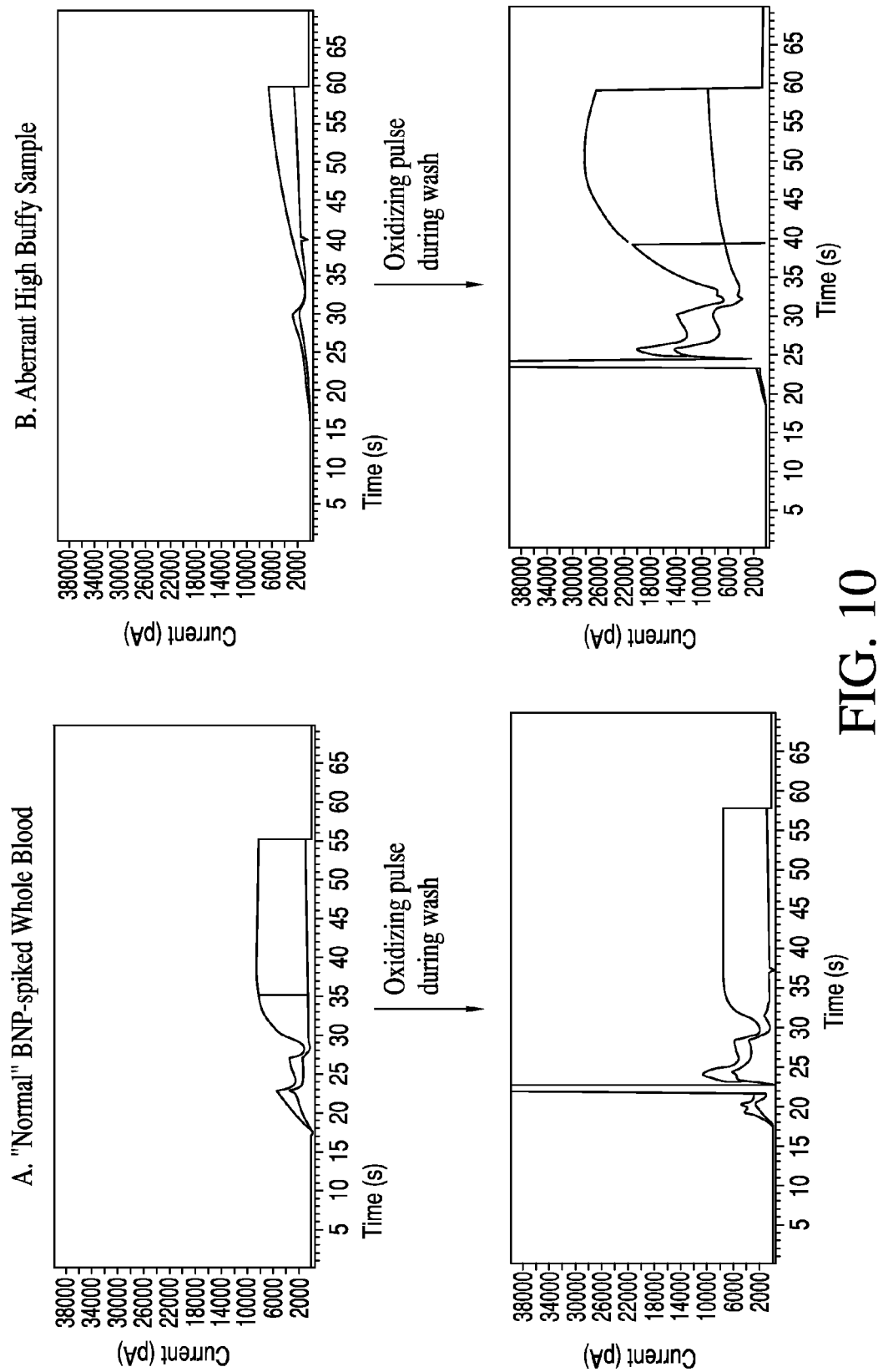
FIG. 10 shows the effect of oxidative electrode pulsing during the wash step on (a) a normal sample, and (b) an aberrant buffy sample.
Figure 11:
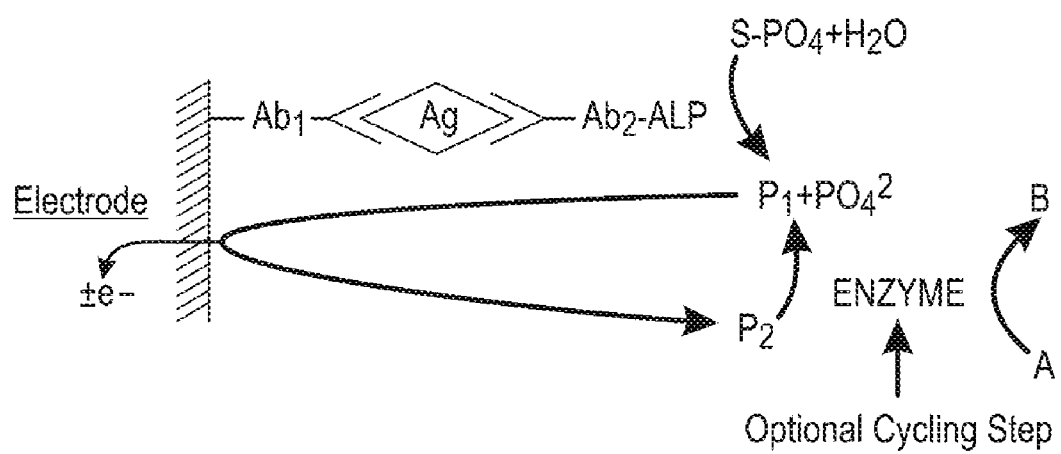
FIG. 11 is a schematic illustration of enzymatic regeneration of an electroactive species.

The conception that the observed interference is associated with an incomplete wash step due to "plugging" or "fouling" of the print layer was assessed further by applying a pulse to extreme potentials, e.g., applying a pulse to an oxidizing potential, during the wash step. It was anticipated that positively sloping waveforms might be caused by an inactive blocked sensor and that pulsing might be employed to clean the electrode prior to the analysis step. It was observed that applying an oxidizing pulse during the wash step in a normal sample had no effect on observed signal and in the subsequent analysis. See FIG. 10(a). However, in the case of aberrant high buffy samples the effect of pulsing was large and dynamic signals and further, these signals were greater than expected given the concentration of analyte. See FIG. 10(b).

The difference in the response to an oxidizing potential pulse in these two cases demonstrated that the fluids within the sensor structure were indeed different. As anticipated, the correct response resulted from the presence of desired analysis fluid over the sensor, whereas the abnormal response arose because the fluid over the sensor structure was plasma, or a combination of plasma and analysis fluid. The difference in response can be understood as follows: the oxidizing pulse results in the evolution of oxygen and a decrease in pH according to: $H_2O \rightarrow \frac{1}{2}O_2 + 2H^+ + 2e^-$.

In the case of the sensor structure containing analysis fluid buffered to pH 9.2, protons evolved at the electrode were rapidly consumed in the presence of the buffer (100 mM carbonate in analysis fluid). However, in the absence of the buffering afforded by the analysis fluid, protons persisted in the region of the electrode resulting in a plume of acidic fluid. This acidic plume resulted in the acid-catalyzed hydrolysis of p-aminophenyl phosphate (p-APP) to para-aminophenol (p-AP) generating a larger signal than anticipated. Specifically, the aberrant waveform arose from p-AP generated by the enzymatic action of the enzyme, e.g., ALP, on p-APP and also non-enzymatic acid-catalyzed hydrolysis.

It is noted that the acid-catalyzed hydrolysis reaction does not occur significantly for pAPP unless the amino group is protonated, as it is at low pH. This is because the reaction requires a strongly electron-withdrawing substituent in the para position (See, e.g., Barnard et al., J. Chem. Soc. (1966), 227-235). As is known in the art, an —$NH_2$ substituent is significantly electron-donating, whereas upon protonation the —$NH_3^+$ substituent becomes highly electron-withdrawing (more so even than —$NO_2$. For example, the Hammet para-rho values are –0.66 for —$NH_2$ and 1.70 for —$NH_3^+$).

These experiments associated the observed interference with "high buffy" samples and could intentionally be elicited by running whole blood samples with an "enriched buffy coat." This term is given to the layer of white blood cells and platelets that form at the plasma-red cell boundary when a blood sample is centrifuged. Further evidence implicating leukocytes and potentially platelets as fouling agents is shown in the micrographs FIGS. 14(a) (assay without use of sacrificial beads or leukocidal reagent) and 14(b) (assay after using non-magnetic sacrificial beads). For comparison, a pristine immunosensor prior to contact with a blood sample is illustrated in FIG. 17. Similar results were obtained providing visual confirmation that magnetic beads can be localized away from the area where the immunosensor is located.

Figure 14A:
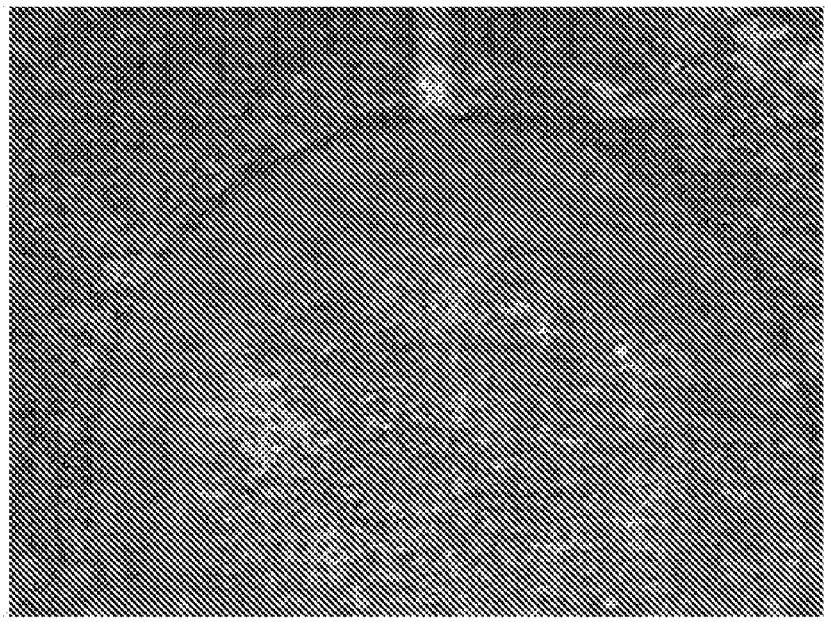
FIG. 14($a$) and ($b$) show micrographs of immunosensors after assay of BNP in a high buffy sample in the (a) absence and (b) presence of sacrificial beads in the sample.

FIG. 14(a) shows a sensor that was exposed to a high buffy sample (~$10^5$ leukocytes per µL) using the standard measurement cycle with a sensor incubation time of 10 minutes. The sample was not exposed to opsonized sacrificial beads. It is clear that a portion of the assay bead-coated sensor surface is covered with an adhered layer of cells that were not easily removed by the wash step.

Figure 14B:
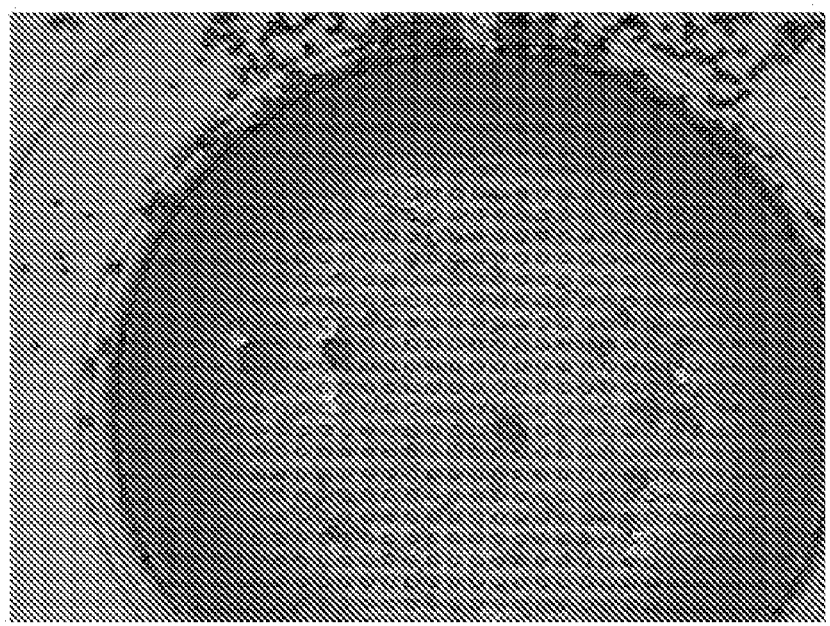

By contrast, FIG. 14(b) shows a sensor that was exposed to a high buffy sample (~$10^5$ leukocytes per µL) using the standard measurement cycle with a sensor incubation time of 10 minutes. However, in contrast to the assay shown in FIG. 14(a), the sample shown in FIG. 14(b) was exposed to opsonized (IgG coated) sacrificial beads (which were non-magnetic). It is clear that the portion of the assay bead-coated sensor surface had significantly less adhered cells when compared to FIG. 14(a) after the wash step.

IgG acts as an opsonin, which is a substance capable of marking a pathogen for phagocytosis, for example, by leukocytes. IgGs are generally added to immunoassays to manage heterophile antibody interference as described in jointly-owned pending U.S. application Ser. No. 12/411,325, and are present on the immobilized assay beads (microparticles) in the BNP cartridge described herein. Consequently, it is likely that either this source of IgG (when present in an immunoassay device) or IgG naturally present in the blood sample may act to undesirably opsonize the sensor surface to leukocytes. In addition, as the assay beads are similar in size to biological cells (bacteria), which are the natural target of phagocytosis, it is probable that IgG accumulation on the assay beads is undesirably promoting accumulation of leukocytes on these beads. This is consistent with the observed interference in samples with high white cell counts, and possibly those with an activated immune status. The present invention provides a solution to this leukocyte interference whereby the amendment of a sample with sacrificial IgG-coated magnetic beads affords a means for decreasing leukocyte activity so as to divert them from the primary immune reagents on the sensor.

In some embodiments of the invention, preparation of IgG-coated immobilized assay beads (microparticles) involves adsorption of IgG onto carboxylated polystyrene immobilized microparticles in MES buffer (2-(N-morpholino) ethanesulfonic acid) followed by cross-linking in the presence of EDAC (1-ethyl-3-(3-dimethylaminopropyl) carbodiimide). However, the immobilized assay beads can be comprised of any suitable material known the art.

One non-limiting method for forming the immobilized assay beads (microparticles) is now described. In one procedure, raw immobilized microparticles are pelleted by centrifugation at 18,000 RCF (relative centrifugal force) for 20 minutes from their matrix (10% microparticles in water, Seradyn) and re-suspended in 25 mM MES buffer to a concentration of 100-200 mg/mL microparticles. IgG dissolved in 25 mM MES buffer is then added in a quantity equal to about 1 to 5% of the weight of the microparticles. After a 15-20 minutes nutation in a refrigerator, the microparticles are pelleted by centrifugation for 20 minutes at 1300 RCF is re-suspended in fresh MES buffer to a concentration of 75 mg/mL. The supernatant from centrifugation is assayed for protein content by measuring absorbance at 280 nm (effective extinction coefficient of 1.4 AU/mg/mL protein) to confirm the IgG has absorbed onto the microparticles. Freshly prepared EDAC cross-linking agent (10 mM in MES buffer) is added to the re-suspended microparticles to a final concentration of about 2-4 mM. The mixture is then stirred by nutation in a refrigerator for 120±15 minutes. The microparticles may then again be pelletized by centrifugation at 1300 RCF for 20 minutes and re-suspended in ⅕ PPS (phosphate buffered saline) and nutated in the refrigerator for 15-30 minutes. Upon final centrifugation, the microparticles can be re-suspended in PBS+0.05% sodium azide or in 1:1 ⅕ PPB: PSS (⅕ PPB is PBS diluted with 4 parts water, PSS=protein stabilization solution, Applied Enzyme Technologies, Pontypool, UK) to a concentration of 10% solids. The resulting preparation may be aliquoted and stored frozen, preferably at −60° C. Microparticles and (non-magnetic) sacrificial beads suspended in PBS formed by this process were employed in the experiments described herein and were dosed directly into blood samples.

While certain assays described above use an immobilized first antibody attached to immobilized assay beads (microparticles), which are in turn attached to a porous layer with an underlying electrode, the first antibody may be immobilized directly onto an electrode or any other surface, or immobilized on a soluble bead.

An exemplary preparation method for an enriched or high buffy whole blood sample (EBS), as described for use in the experiments described herein, was as follows.

In a preferred procedure, fresh whole blood was drawn from a donor into two 6 mL EDTA-anticoagulated Vacutainers® and was centrifuged for 10 minutes at 2000 RCF (standard rotor). Where BNP "positive" samples were desired, the tubes were spiked with the BNP antigen prior to centrifugation. All of the plasma except the last millimeter above the plasma/buffy coat/red blood cell interface was withdrawn and set aside. The interfacial region was withdrawn using a pipette (with the intention of removing as much of the buffy coat layer as possible) and was set aside. The red blood cells were then removed and set aside. By recombining the buffy coat materials with lesser portions of the plasma and red cell fractions, it was possible to create high buffy blood samples while retaining a normal sample hematocrit, e.g., 35-55 wt. %. Similarly, samples with a low or essentially no buffy material (leukocytes and platelets) present can be created.

In experiments, BNP test cartridges were tested with: (i) high buffy samples, (ii) high buffy samples treated with a 10 percent volume a suspension of 10 weight percent microparticles coated with IgG (μP-IgG) in PBS immediately before running, (iii) high hematocrit leukocyte-free samples, and (iv) low hematocrit leukocyte-free samples.

Figure 18:
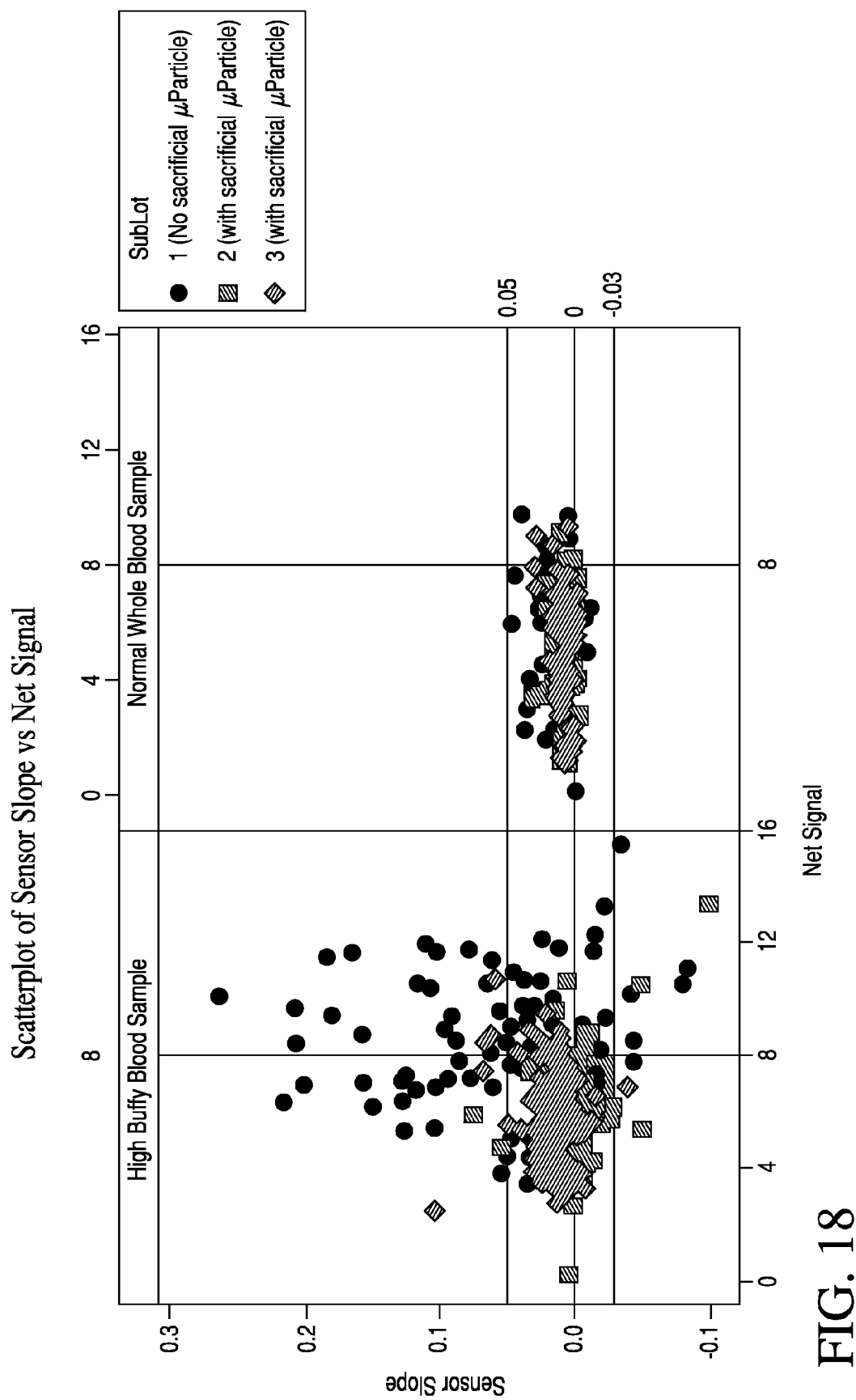
FIG. 18 shows graphical data for the effect on immunosensor slope in high buffy (left panel) and normal whole blood (right panel) samples with (sublots 2 and 3) and without (sublot 1) sacrificial microparticles incorporated in the reagent.

FIG. 18 contains graphical data illustrating the effect of leukocyte interference on electrochemical immunosensor signal slopes and the effect of (non-magnetic) sacrificial bead treatment on the slopes. Illustrated in the right and left panels are Sensor Slopes (y-axis) plotted as a function of Net Signal (x-axis) for normal whole blood sample (right panel) and high buffy blood sample (enriched leukocyte, high buffy, left panel). The left panel illustrates the considerable variability of signal slopes observed in high buffy samples in the absence of sacrificial beads (Sublot 1). This variability was substantially ameliorated in the presence of non-magnetic sacrificial beads (Sublots 2 and 3). Minimal signal slope variability was observed in the normal whole blood samples (right panel) both with and without sacrificial beads. The same or better effect should be realized by using magnetic sacrificial beads according to the present invention.

Figure 19:
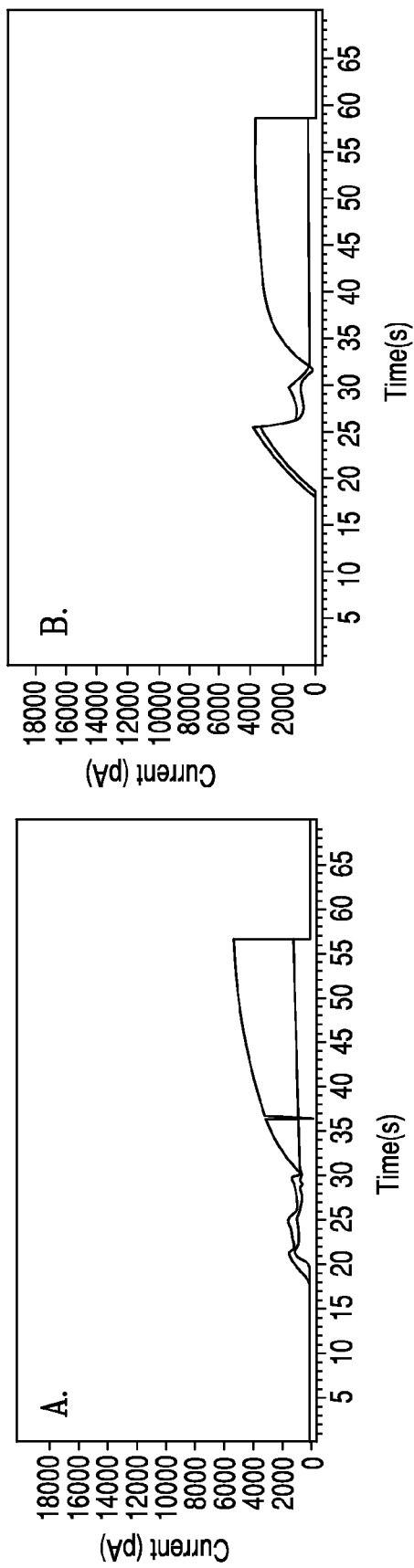
FIG. 19($a$) and ($b$) show analyzer waveforms for the associated immunosensor micrographs in FIG. 14($a$) and ($b$)
Figure 20:
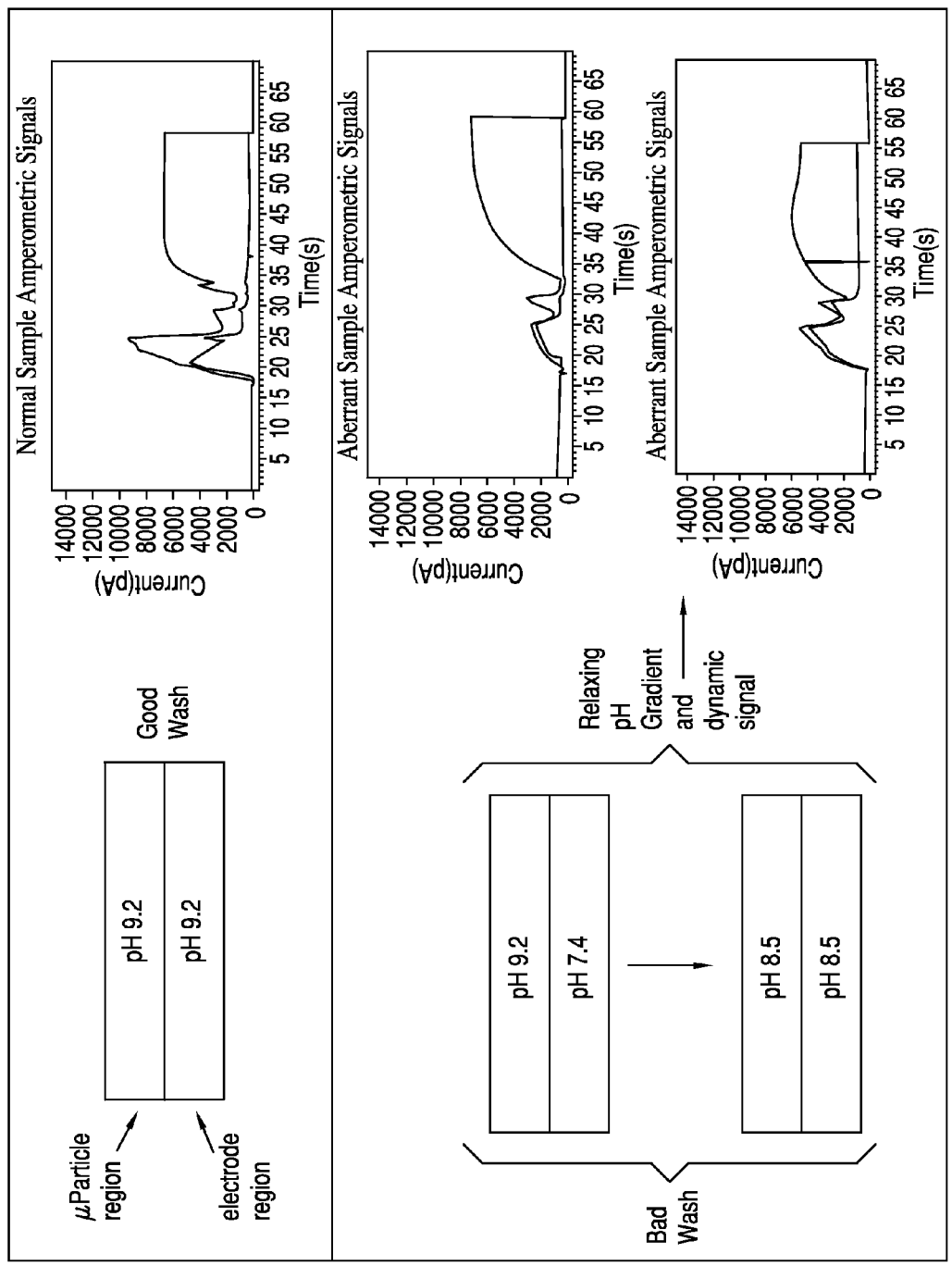
FIG. 20 illustrates the effect of poor washing (inability to replace sample fluid within sensor structure with analysis fluid) on amperometric waveforms.

Microscopic inspection of sensors following the assay revealed the presence of a thick deposit on chips run in high buffy (HB) and the absence of a deposit on samples run in HB/μP-IgG. Micrographs of the immunosensors are shown in FIGS. 14(a) and 14(b) and their associated analyzer waveforms are illustrated in FIGS. 19(a) and (b), respectively. It is clear from a comparison of a pristine immunosensor prior to contact with a blood sample as illustrated in FIG. 17 with the immunosensor after contact with blood treated with the sacrificial beads (FIG. 14(b)) that visually there is a significant improvement, i.e., a reduction in adhered leukocytes compared to FIG. 14(a). Based on many observations, this visual improvement correlates directly with an actual improvement in immunosensor performance. Again, the same or better effects should be obtainable using magnetic sacrificial microparticles according to the present invention.

Additional experiments showed that the interference phenomenon does not occur in plasma alone or in samples containing platelets but not leukocytes, but only in samples containing a high buffy level. In addition, smaller beads, e.g., those having an average particle size less than 0.2 μm, coated with IgG do not have the same interference reduction or elimination effect on sensor slopes as do larger particles. Collectively, the experimental data support the conclusion that leukocytes are primarily responsible for a phenomenon in which the sensor becomes less permeable in the wash cycle and that this immunoassay interference can be ameliorated by addition of sacrificial IgG coated particles to the assay medium.

Figure 7:
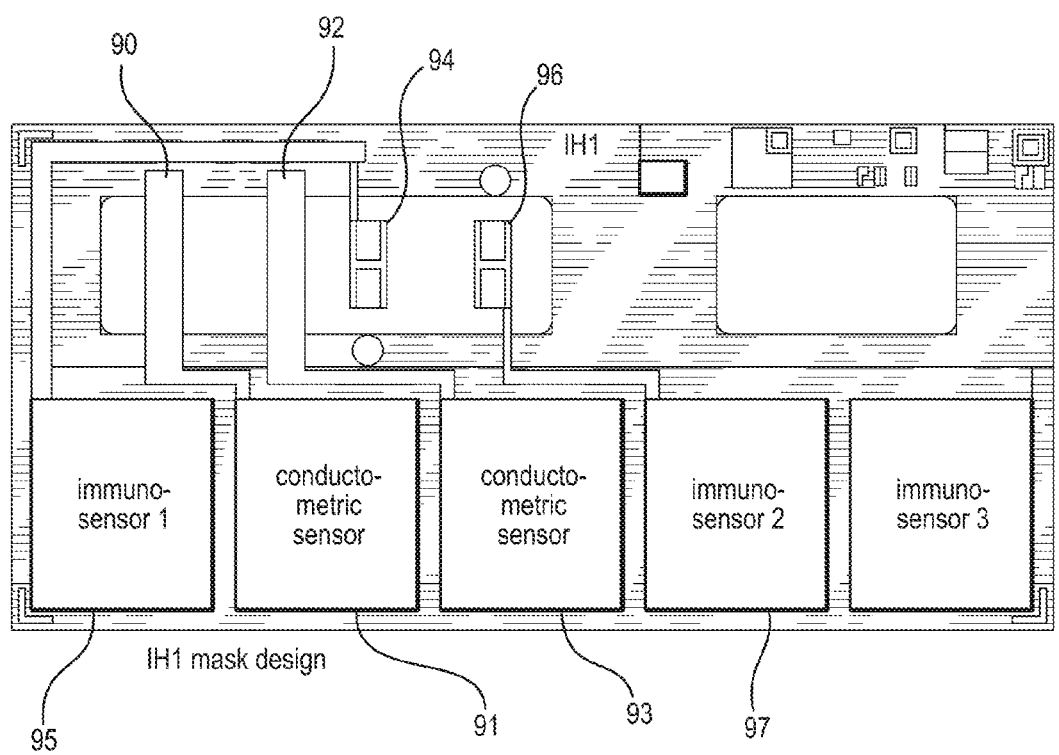
FIG. 7 is a top view of the mask design for the conductimetric and immunosensor electrodes for an immunosensor cartridge according to one embodiment of the invention.

Wafer-level microfabrication of a preferred embodiment of the immunosensor of the present invention is as follows. FIG. 7 illustrates a mask design for several electrodes upon a single substrate. By masking and etching techniques, independent electrodes and leads can be deposited. Thus, a plurality of immunosensors, 94 and 96, and conductimetric sensors, 90 and 92, are provided in a compact area at low cost, together with their respective connecting pads, 91, 93, 95, and 97, for effecting electrical connection to the reading apparatus. In principle, a very large array of sensors can be assembled in this way, each sensitive to a different analyte or acting as a control sensor or reference immunosensor.

In specific embodiments of the invention, immunosensors may be prepared as follows. Silicon wafers are thermally oxidized to form an insulating oxide layer approximately 1 micron thick. A titanium/tungsten layer is sputtered onto the oxide layer to a preferable thickness of between 100 to 1000 Angstroms, followed by a layer of gold that is most preferably 800 Angstroms thick. Next, a photoresist is spun onto the wafer and is dried and baked appropriately. The surface is then exposed using a contact mask, such as a mask corresponding to that illustrated in FIG. 7. The latent image is developed, and the wafer is exposed to a gold-etchant. The patterned gold layer is coated with a photodefinable polyimide, suitably baked, exposed using a contact mask, developed, cleaned in an $O_2$ plasma, and preferably imidized at 350° C. for 5 hours. An optional metallization of the back side of the wafer may be performed to act as a resistive heating element, where the immunosensor is to be used in a thermostatted format. The surface is then printed with antibody-coated beads. Droplets, preferably of about 20 mL volume and containing 1% solid content in deionized water, are deposited onto the sensor region and are dried in place by air drying. Optionally, an antibody stabilization reagent (supplied by SurModica Corporation, Eden Prairie, Minn., USA or Applied Enzyme Technology Ltd, Pontypool, UK) is overcoated onto the sensor.

Drying the particles causes them to adhere to the surface in a manner that prevents dissolution in either sample or fluid containing a substrate. This method provides a reliable and reproducible immobilization process suitable for manufacturing sensor chips in high volume.

As shown in FIG. 7, the base electrode 94 comprises a square array of 7 μm gold disks on 15 μm centers. The array covers a circular region approximately 600 μm in diameter, and is achieved by photo-patterning a thin layer of polyimide of thickness 0.35 μm over a substrate made from a series of layers comprising $Si/SiO_2/TiW/Au$. The array of 7 μm microelectrodes affords high collection efficiency of electroactive species with a reduced contribution from any electrochemical background current associated with the capacitance of the exposed metal. The inclusion of a poly(vinyl alcohol) (PVA) layer over the metal significantly enhances the reduction of background currents.

In some embodiments, the porous PVA layer is prepared by spin-coating an aqueous mixture of PVA plus a stilbizonium photoactive, cross-linking agent over the microelectrodes on the wafer. The spin-coating mixture optionally includes bovine serum albumin (BSA). The wafer is then photo-patterned to cover only the region above and around the arrays and preferably has a thickness of about 0.6 µm.

The general concept of differential measurement is known in the electrochemical and sensing arts. A novel means for reducing interfering signals in electrochemical immunosensing systems is now described. While it is described for pairs of amperometric electrochemical sensors, it is of equal utility in other electrochemical sensing systems including, but not limited to potentiometric sensors, field effect transistor sensors and conductimetric sensors. Embodiments of the present invention are also applicable to optical sensors, e.g., evanescent wave sensors and optical wave guides, and also other types of sensing including acoustic wave and thermometric sensing and the like. Thus, according to various embodiments of the invention, the immobilized antibody may be attached to a sensor selected from the group consisting of an amperometric electrode, a potentiometric electrode, a conductimetric electrode, an optical wave guide, a surface plasmon resonance sensor, an acoustic wave sensor and a piezoelectric sensor.

Ideally, in the non-competitive assay embodiments, the signal from an immunosensor (IS) is derived solely from the formation of a sandwich comprising an immobilized antibody (Ab1), the analyte, and a signal antibody (Ab2) that is labeled, wherein the label (e.g., an enzyme) reacts with a substrate (S) to form a detectable product (P) as shown below in scheme (1).

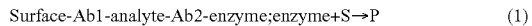

Surface-Ab1-analyte-Ab2-enzyme;enzyme+S→P    (1)

It is known that some of the signal antibody (Ab2) may bind non-specifically to the surface, as shown below in schemes (2) and (3), and might not be washed away completely from the region of the immunosensor (up to approx. 100 microns away) during the washing step thereby giving rise to a portion of the total detected product that is not a function of the surface-Ab1-analyte-Ab2-enzyme immunoassay sandwich structure, thereby creating an interfering signal.

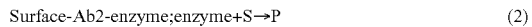

Surface-Ab2-enzyme;enzyme+S→P    (2)

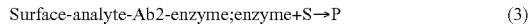

Surface-analyte-Ab2-enzyme;enzyme+S→P    (3)

As indicated above, a second immunosensor optionally may be placed in the cartridge that acts as an immuno-reference sensor (IRS) and gives the same (or a predictably related) degree of non-specific binding (NSB) as occurs on the primary immunosensor. In one embodiment, interference can be reduced by subtracting the signal of this immuno-reference sensor from that of the primary immunosensor, i.e., the NSB component of the signal is removed, improving the performance of the assay, as shown in scheme (4) below. In another embodiment, the correction may optionally include the subtraction or addition of an additional offset value.

Corrected signal=IS−IRS    (4)

In preferred embodiments of the invention, the reference immunosensor, also referred to as immuno-reference sensor, is the same in all significant respects (e.g., dimensions, porous screening layer, latex particle coating, and metal electrode composition) as the primary immunosensor except that the capture antibody for the analyte (e.g., cTnI) is replaced by an antibody to a plasma protein that naturally occurs in samples (both normal and pathological) at a high concentration. The immunosensor and reference immunosensor may be fabricated as adjacent structures 94 and 96, respectively, on a silicon chip as shown in FIG. 7. While the preferred embodiment is described for troponin I and brain natriuretic peptide (BNP) assays, this structure is also useful for other cardiac marker assays including, for example, troponin T, creatine kinase MB, procalcitonin, proBNP, NTproBNP, myoglobin and the like, plus other sandwich assays used in clinical diagnostics, e.g., PSA, D-dimer, CRP, HCG, NGAL, myeloperoxidase and TSH.

Examples of suitable antibodies that bind to plasma proteins include antibodies to human serum albumin, fibrinogen and IgG fc region, with human serum albumin being preferred. However, any native protein or blood component that occurs at a concentration of greater than about 100 ng/mL can be used if an appropriate antibody is available. The protein should, however, be present in sufficient amounts to coat the sensor quickly relative to the time needed to perform the analyte assay. In a preferred embodiment, the protein is present in a blood sample at a concentration sufficient to bind more than 50% of the available antibody on the reference immunosensor within about 100 seconds of contacting a blood sample. In general, the second immobilized antibody has an affinity constant of about $1\times10^{-7}$ to about $1\times10^{-15}$ M. For example, an antibody to albumin having an affinity constant of about $1\times10^{-10}$ M is preferred, due to the high molar concentration of albumin in blood samples, which is about $1\times10^{-4}$ M.

According to various embodiments of the present invention, providing a surface that is covered by native albumin derived from the sample significantly reduces the binding of other proteins and cellular materials that may be present. This method is generally superior to conventional immunoassays that use conventional blocking agents to minimize NSB because these agents must typically be dried down and remain stable for months or years before use, during which time they may degrade, creating a stickier surface than desired and resulting in NSB that increases with age. In contrast, embodiments of the present invention provide for a fresh surface at the time of use.

One embodiment of an immunosensor for BNP with a reference immunosensor for performing differential measurement to reduce the effect of NSB is described as follows. In one embodiment, assay beads (microparticles) comprising carboxylate-modified latex microparticles (supplied by Bangs Laboratories Inc., Fishers, Ind., USA or Seradyn Inc., Indianapolis, Ind., USA) coated with anti-BNP and anti-human serum albumin (HSA) are both prepared by the same method. The assay beads are first buffer exchanged by centrifugation, followed by addition of the antibody, which is allowed to passively adsorb onto the beads. The carboxyl groups on the assay beads are then activated with (1-ethyl-3-(3-dimethylaminopropyl)carbodiimide) (EDAC) in MES buffer (2-(N-morpholino)ethanesulfonic acid) at pH 6.2, to form amide bonds to the antibodies. Any bead aggregates are removed by centrifugation and the finished beads are stored frozen.

In another embodiment, the anti-HSA antibody saturation coverage of the beads results in about a 7% increase in bead mass. In yet another embodiment, coated beads are prepared using covalent attachment from a mixture comprising 7 mg of anti-HSA and 100 mg of beads. Using this preparation, a droplet of about 0.4 mL, comprising about 1% solids in deionized water, is microdispensed (using the method and apparatus of U.S. Pat. No. 5,554,339, referenced above and incorporated herein by reference in its entirety) onto a photo-patterned porous PVA permselective layer covering sensor 96, and is allowed to dry. The dried particles adhere to the porous layer and substantially prevent their dissolution in the blood sample or the washing fluid.

In one embodiment of the invention, for the BNP antibody, saturation coverage of the bead surface results in a mass increase in the beads of about 10%. Thus by adding 10 mg of anti-BNP to 100 mg of beads along with the coupling reagent, saturation coverage was achieved. These beads were then microdispensed onto sensor 94.

In yet another embodiment, immunosensor 94 is coated with assay beads having both a plasma protein antibody, e.g., anti-HSA, and the analyte antibody, e.g., anti-BNP. Beads made with about 2 mg or less of anti-HSA per 100 mg of beads saturation-coated with anti-BNP provide superior NSB properties at the immunosensor. It has been found that the slope (signal versus analyte concentration) of the troponin assay is not materially affected because there is sufficient anti-BNP on the bead to capture the available analyte (antigen). By determining the bead saturation concentration for different antibodies, and the slope of an immunosensor having beads with only the antibody to the target analyte, appropriate ratios of antibody combinations can be determined for beads having antibodies to both a given analyte and a plasma protein.

An important aspect of immunosensors having a reference immunosensor is the "humanizing" of the surface created by a layer of plasma protein, preferably the HSA/anti-HSA combination. This surface "humanizing" appears to make the beads less prone to NSB of the antibody-enzyme conjugate and also seems to reduce bead variability. Without being bound by theory, it appears that as the sensors are covered by the sample they are rapidly coated with native albumin due to the anti-HSA surface. This gives superior results compared to conventional blocking materials, which are dried down in manufacturing and re-hydrated typically after a long period in storage. Another advantage to "humanizing" the sensor surface is that it provides an extra mode of resistance to human anti-mouse antibodies (HAMA) and other heterophile antibody interferences. The effects of HAMA on immunoassays are well known.

In another embodiment, the immuno-reference sensor is employed in the devices and methods of the invention to monitor the wash efficiency obtained during the analytical cycle. As stated above, one source of background noise is the small amount of enzyme conjugate still in solution, or non-specifically absorbed on the sensor and not removed by the washing step. This aspect of the invention relates to performing an efficient washing step using a small volume of washing fluid, by introducing air segments as described herein.

In operation of the preferred embodiment, which is an amperometric electrochemical system, the currents associated with oxidation of p-aminophenol at immunosensor 94 and immuno-reference sensor 96 arising from the activity of ALP, are recorded by the analyzer. The potentials at the immunosensor and immuno-reference sensor are poised at the same value with respect to a silver-silver chloride reference electrode. To remove the effect of interference, the analyzer subtracts the signal of the immuno-reference sensor from that of the immunosensor according to equation (4) above. Where there is a characteristic constant offset between the two sensors, this value is also subtracted. It is not necessary for the immuno-reference sensor to have all of the same non-specific properties as the immunosensor, only that the immuno-reference sensor be consistently proportional in both the wash and NSB parts of the assay. In one embodiment, an algorithm embedded in the analyzer can account for any other essentially constant difference between the two sensors.

Use of a differential combination of immunosensor and immuno-reference sensor, rather than an immunosensor alone, provides the following improvement to the assay. In a preferred embodiment, the cartridge design provides dry reagent that yields about 4-5 billion enzyme conjugate molecules dissolved into about a 10 µL blood sample. At the end of the binding and wash steps the number of enzyme molecules at the sensor is about 70,000. In experiments with the preferred embodiment there were, on average, about 200,000 (±about 150,000) enzyme molecules on the immunosensor and the reference immunosensor as non-specifically bound background. Using a differential measurement with the immuno-reference sensor, about 65% of the uncertainty was removed, significantly improving the performance of the assay. While other embodiments may have other degrees of improvement, the basis for the overall improvement in assay performance remains.

An additional use of the optional immuno-reference sensor is to detect anomalous sample conditions, such as for example improperly anti-coagulated samples which deposit material throughout the conduits and cause increased currents to be measured at both the immunosensor and the immuno-reference sensor. This effect is associated with both non-specifically adsorbed enzyme and enzyme remaining in the thin layer of wash fluid over the sensor during the measurement step.

Another use of the optional immuno-reference sensor is to correct signals for washing efficiency. In certain embodiments, the level of signal at an immunosensor depends on the extent of washing. For example, longer washing with more fluid/air segment transitions can give a lower signal level due to a portion of the specifically bound conjugate being washed away. While this may be a relatively small effect, e.g., less than 5%, correction can improve the overall performance of the assay. Correction may be achieved based on the relative signals at the sensors, or in conjunction with a conductivity sensor located in the conduit adjacent to the sensors, acting as a sensor for detecting and counting the number of air segment/fluid transitions. This provides the input for an algorithmic correction means embedded in the analyzer.

In another embodiment of the reference immunosensor with an endogenous protein, e.g., HSA, it is possible to achieve the same goal by having an immuno-reference sensor coated with antibody to an exogenous protein, e.g., bovine serum albumin (BSA). In this case, the step of dissolving a portion of the BSA in the sample, provided as an additional reagent, prior to contacting the sensors is necessary. This dissolution step can be done with BSA as a dry reagent in the sample holding chamber of the cartridge, or in an external collection device, e.g., a BSA-coated syringe. This approach offers certain advantages, for example the protein may be selected for surface charge, specific surface groups, degree of glycosylation and the like. These properties may not necessarily be present in the available selection of endogenous proteins.

In addition to salts, other reagents can improve whole-blood precision in an immunoassay. These reagents should be presented to the blood sample in a way that promotes rapid dissolution. In some embodiments, support matrices including cellulose, polyvinyl alcohol (PVA), and gelatin (or mixtures thereof) coated onto the wall of the blood-holding chamber (or another conduit) promote rapid dissolution, e.g., greater than 90% complete in less than 15 seconds.

In another embodiment, analyte measurements are performed in a thin-film of liquid coating an analyte sensor. Such thin-film determinations are preferably performed amperometrically. This cartridge differs from the foregoing embodiments in having both a closeable valve that is sealed when the sample is expelled through the valve, and an air vent within the conduits that permits at least one air segment to be subsequently introduced into the measuring fluid, thereby increasing the efficiency with which the sample is rinsed from the sensor, and further permitting removal of substantially all the liquid from the sensor prior to measurement, and still further permitting segments of fresh liquid to be brought across the sensor to permit sequential, repetitive measurements for improved accuracy and internal checks of reproducibility.

In non-competitive assay embodiments, as discussed above, the analysis scheme for the detection of low concentrations of immunoactive analyte relies on the formation of an enzyme labeled antibody/analyte/surface-bound antibody "sandwich" complex. The concentration of analyte in a sample is converted into a proportional surface concentration of an enzyme. The enzyme is capable of amplifying the analyte's chemical signal by converting a substrate to a detectable product. For example, where alkaline phosphatase is the enzyme, a single enzyme molecule can produce about nine thousand detectable molecules per minute, providing several orders of magnitude improvement in the detectability of the analyte compared to schemes in which an electroactive species is attached to the antibody in place of alkaline phosphatase.

In immunosensor embodiments, it is advantageous to contact the sensor first with a sample and then with a wash fluid prior to recording a response from the sensor. In some specific embodiments, in addition to being amended with an IgG-coated microparticle in order to reduce leukocyte interference, the sample is amended with an antibody-enzyme conjugate (signal antibody) that binds to the analyte of interest within the sample before the amended sample contacts the sensor. Binding reactions in the sample produce an analyte/antibody-enzyme complex. The sensor comprises an immobilized antibody to the analyte, attached close to an electrode surface. Upon contacting the sensor, the analyte/antibody-enzyme complex binds to the immobilized antibody near the electrode surface. It is advantageous at this point to remove from the vicinity of the electrode as much of the unbound antibody-enzyme conjugate as possible to minimize background signal from the sensor. The enzyme of the antibody-enzyme complex is advantageously capable of converting a substrate, provided in the fluid, to produce an electrochemically active species. This active species is produced close to the electrode and provides a current from a redox reaction at the electrode when a suitable potential is applied (amperometric operation). Alternatively, if the electroactive species is an ion, it can be measured potentiometrically. In amperometric measurements the potential may either be fixed during the measurement, or varied according to a predetermined waveform. For example, a triangular wave can be used to sweep the potential between limits, as is used in the well-known technique of cyclic voltammetry. Alternatively, digital techniques such as square waves can be used to improve sensitivity in detection of the electroactive species adjacent to the electrode. From the current or voltage measurement, the amount or presence of the analyte in the sample is calculated. These and other analytical electrochemical methods are well known in the art.

In embodiments in which the cartridge comprises an immunosensor, the immunosensor is advantageously microfabricated from a base sensor of an unreactive metal such as gold, platinum or iridium, and a porous permselective layer that is overlaid with a bioactive layer attached to a microparticle, e.g., latex beads. The microparticles are dispensed onto the porous layer covering the electrode surface, forming an adhered, porous bioactive layer. The bioactive layer has the property of binding specifically to the analyte of interest, or of manifesting a detectable change when the analyte is present, and is most preferably an immobilized antibody directed against the analyte.

IX. Devices, Kits and Methods for Reducing or Eliminating Leukocyte Interference The present invention is applicable to both sandwich and competitive immunoassays. In sandwich assay embodiments, the sample contacts an immunosensor with an immobilized first antibody to the target analyte, and a labeled second antibody to said target analyte. In competitive assay embodiments, the sample contacts an immunosensor comprising an immobilized first antibody to said target analyte, and a labeled target analyte that competes for binding with the target analyte. Typical analytes include, but are not limited to TnI, TnT, BNP, NTproBNP, proBNP, HCG, TSH, NGAL, digoxin, theophylline and phenyloin and the like.

In some embodiments of the invention, the sample, e.g., whole blood sample, is first collected and then amended by dissolving a dry reagent comprising magnetic sacrificial beads into the sample. In certain embodiments, sufficient sacrificial beads are utilized to provide an excess of beads with respect to leukocytes in the sample. This yields a sample with a dissolved sacrificial bead concentration of at least 5 µg per µL of sample, e.g., at least 10 µg per µL of sample, or at least 15 µg per µL of sample, which is sufficient to substantially engage any leukocytes in the sample. In terms of ranges, the dry reagent preferably dissolves into the sample to give a sacrificial bead concentration of from about 5 µg to about 40 µg beads per µL of sample, preferably from about 10 to about 20 µg beads per µL of sample. Depending on the size of the beads, this corresponds to at least about $10^4$ beads per µL of sample, at least about $10^5$ beads per µL of sample, or approximately from about $10^5$ to about $10^6$ beads per µL of sample. Thus, in some preferred embodiments, the sacrificial beads are present in an amount sufficient to provide a dissolved sacrificial bead concentration of at least $10^4$ beads per µL of sample, e.g., at least about $10^5$ beads per µL of sample, or from about $10^5$ to about $10^6$ beads per µL of sample. Once this step is completed, it is possible to perform an immunoassay, e.g., an electrochemical immunoassay, on the amended sample to determine the concentration of an analyte.

The dissolution of the dry reagents and the sandwich formation step can occur concurrently or in a stepwise manner. Embodiments of the method of the present invention are directed mainly to analytes that are cardiovascular markers, e.g., TnI, TnT, CKMB, myoglobin, BNP, NT-proBNP, and proBNP, but can also be used for other markers such as, for example, beta-HCG, TSH, myeloperoxidase, myoglobin, D-dimer, CRP, NGAL and PSA. To ensure that the majority of the leukocytes are sequestered before the detection step, it is preferable that the sample amendment step is for a selected predetermined period in the range of about 1 minute to about 30 minutes.

In preferred embodiments, the method is performed in a cartridge comprising an immunosensor, a conduit, a sample entry port and a sample holding chamber, where at least a portion of at least one of these elements is coated with the dry reagent. The dry reagent can include one or more of: magnetic sacrificial beads for reducing leukocyte interference, a leukocidal reagent, buffer, salt, surfactant, stabilizing agent, a simple carbohydrate, a complex carbohydrate and various combinations. In addition, the dry reagent can also include an enzyme-labeled antibody (signal antibody) to the analyte.

Prior to the assaying step, a magnetic field is applied to the magnetic sacrificial beads in order to retain them along with any associated leukocytes onto a surface of the cartridge, e.g., onto a conduit of the cartridge, and substantially out of contact from the immunosensor.

In the actual assay step, in preferred embodiments, once the sandwich is formed between the immobilized and signal antibodies, the sample medium is subsequently washed to a waste chamber, followed by exposing the sandwich to a substrate capable of reacting with an enzyme to form a product capable of electrochemical detection. The preferred format is an electrochemical enzyme-linked immunosorbent assay.

Certain embodiments of the invention are directed to a kit for performing an immunoassay that comprises the magnetic sacrificial beads. The kit or method is applicable to any sample containing leukocytes, e.g., whole blood, and can be a blood sample amended with an anticoagulant, e.g., EDTA, heparin, fluoride, citrate and the like.

In some embodiments, the magnetic sacrificial beads are used to amend the biological sample, e.g., blood, in a first container or location, and then the sample is passed to a second container or location which has the capture and signal antibodies. In other embodiments, the magnetic sacrificial beads are contained in solution and mixed with the biological sample, and the resulting amended sample is introduced into the analysis device. For example, a blood sample may be mixed with the magnetic sacrificial beads to form an amended sample, which is then introduced into the cartridge. In certain embodiments, the analysis device, e.g., cartridge, includes a pouch that contains a liquid comprising the magnetic sacrificial beads, which may be mixed with a biological sample in the device and then processed substantially as described herein to form an assay, e.g., sandwich assay, for analyte detection.

In other embodiments, electrowetting is employed to mix a first liquid comprising the magnetic sacrificial beads with a liquid biological sample, e.g., blood. In one such embodiment, an apparatus may be provided for manipulating droplets. The apparatus, for example, may have a single-sided electrode design in which all conductive elements are contained on one surface on which droplets are manipulated. In other embodiments, an additional surface is provided parallel with the first surface for the purpose of containing the droplets to be manipulated. The droplets are manipulated by performing electrowetting-based techniques in which electrodes contained on or embedded in the first surface are sequentially energized and de-energized in a controlled manner. The apparatus may allow for a number of droplet manipulation processes, including merging and mixing two droplets together, splitting a droplet into two or more droplets, sampling a continuous liquid flow by forming from the flow individually controllable droplets, and iterative binary or digital mixing of droplets to obtain a desired mixing ratio. In this manner, droplets of the first liquid comprising the magnetic sacrificial beads and optionally one or more leukocidal reagents may be carefully and controllably merged and mixed with the liquid biological sample, e.g., blood. See, e.g., U.S. Pat. No. 6,911,132 to Pamula et al., the entirety of which is incorporated herein by reference.

In addition, a current immunoassay format known in the art may be modified to include the magnetic sacrificial beads of the present invention, for example by adding the beads in a sample pre-treatment step. This pretreatment may be accomplished by incorporating the sacrificial beads in a blood collection device, in a separate vessel, or may take place in the analytical (immunoassay) device itself by incorporation of the sacrificial beads in the test cycle of the device.

While the present invention has been described in the context of a brain natriuretic peptide (BNP) test cartridge, it is equally applicable to any immunoassay where leukocytes are present and can be the cause of interference. Likewise, the method or kit is not limited to BNP but can be adapted to any immunoassay, including but not limited to proBNP, NTproBNP, cTnI, TnT, HCG, TSH, PSA, D-dimer, CRP, myoglobin, NGAL, CKMB, myeloperoxidase and galectin-3. In addition, the method and kit is applicable to assays where the magnetic sacrificial beads are coated with any non-human IgG or a fragment thereof, including murine, caprine, bovine and lupine, and alternatively sacrificial beads coated with an activated human IgG or fragment thereof. The magnetic sacrificial beads may comprise substrate beads coated with a material or fragment thereof selected from a protein, a bacterium, a virus and a xenobiotic, or may be afforded by dormant or otherwise stabilized bacterial cells, spores or fragment thereof, e.g., *E. coli*, optionally without substrate beads.

The kit or method of the present invention can comprise a second labeled antibody that is in the form of a dissolvable dry reagent. In some embodiments, the dissolvable dry reagent includes one or more leukocidal reagents and/or opsonized sacrificial beads as part of the dissolvable dry reagent, or where the various components are in separate dry reagent locations. For a discussion of leukocidal reagents, see co-pending U.S. patent application Ser. No. 12/771,634, the entirety of which is incorporated herein by reference. Note that both the immobilized and labeled antibodies can be monoclonal, polyclonal, fragments thereof and combinations thereof. In addition, the second antibody can be labeled with various labels including a radiolabel, enzyme, chromophore, fluorophore, chemiluminescent species and other known in the immunoassay art. Where the second antibody is labeled with an enzyme, it is preferably ALP, horseradish peroxidase, or glucose oxidase.

Where the method or kit is used to perform a non-competitive immunoassay there may be a sequence of mixing steps including: (i) mixing a blood sample suspected of containing an analyte with reagent including magnetic sacrificial beads opsonized for leukocytes; (ii) allowing the magnetic sacrificial beads to bond to the leukocytes; (iii) magnetically retaining the beads and any associated leukocytes in a magnetic field region; (iv) mixing the blood sample with an immobilized first antibody to the analyte and forming a complex between the immobilized antibody and said analyte; and (v) mixing the blood sample with a labeled second antibody to form a complex with said analyte and said immobilized antibody. Note that these mixing steps can be performed at the same time or in an ordered sequence. For example, steps (iv) and (v) may occur at the same time, or steps (i) and (v) may be performed before step (iv). In the final step there is a determination of the amount of complex formed between the immobilized first antibody, the analyte and the labeled second antibody.

EXAMPLES

The present invention will be better understood in view of the following non-limiting prophetic Examples.

Example 1

In one embodiment, an unmetered fluid sample is introduced into sample holding chamber 34 of a cartridge, through sample entry port 4. Capillary stop 25 prevents passage of the sample into conduit 15 at this stage, and holding chamber 34 is filled with the sample. Lid 2 or element 200 is closed to prevent leakage of the sample from the cartridge. The cartridge is then inserted into a reading apparatus, such as that disclosed in U.S. Pat. No. 5,821,399, which is hereby incorporated by reference. Insertion of the cartridge into a reading apparatus activates the mechanism, which punctures a fluid-containing package located at 42 when the package is pressed against spike 38. Fluid is thereby expelled into the second conduit, arriving in sequence at 39, 20, 12 and 11. The constriction at 12 prevents further movement of fluid because residual hydrostatic pressure is dissipated by the flow of fluid via second conduit portion 11 into the waste chamber 44. In a second step, operation of a pump means applies pressure to air bladder 43, forcing air through conduit 40, through cutaways 17 and 18, and into conduit 34 at a predetermined location 27. Capillary stop 25 and location 27 delimit a metered portion of the original sample. While the sample is within sample holding chamber 34, it is amended with the dry reagent coating comprising magnetic sacrificial beads and optionally non-magnetic sacrificial beads and/or one or more leukocidal reagents and any other desired materials on the inner surface of the chamber. The metered portion of the sample is then expelled through the capillary stop by air pressure produced within air bladder 43. Preferably, the sample is allowed to mix, e.g., in holding chamber 34 and/or conduit 15, with the magnetic sacrificial beads under conditions sufficient (optionally facilitated with oscillation of the sample) to allow leukocytes contained in the sample to bind to the magnetic sacrificial beads. A magnetic field is then applied to the sample in order to retain the magnetic sacrificial beads onto a surface of the conduit and substantially out of contact from the immunosensor. The sample then passes into contact with the analyte sensor or sensors located within cutaway 35.

In embodiments employing an immunosensor located within cutout 35, the sample is amended prior to arriving at the sensor by, for example, an enzyme-antibody conjugate (signal antibody). To promote efficient binding of the analyte to the sensor, the sample containing the analyte is optionally passed repeatedly over the sensor in an oscillatory motion. Preferably, an oscillation frequency of between about 0.2 and 2 Hz is used, most preferably 0.7 Hz. Thus, the signal enzyme associated with the signal antibody is brought into close proximity to the amperometric electrode surface in proportion to the amount of analyte present in the sample.

Once an opportunity for the analyte/enzyme-antibody conjugate complex to bind to the immunosensor has been provided, the sample is ejected by further pressure applied to air bladder 43, and the sample passes to waste chamber 44. A wash step next removes non-specifically bound enzyme-conjugate and sacrificial beads from the sensor chamber. Fluid in the second conduit is moved by a pump means 43, into contact with the sensors. The analysis fluid is pulled slowly until the first air segment is detected at a conductivity sensor.

The air segment or segments can be produced within a conduit by any suitable means, including but not limited to: (1) passive means; (2) active means including a transient lowering of the pressure within a conduit using a pump whereby air is drawn into the conduit through a flap or valve; or (3) by dissolving a compound pre-positioned within a conduit that liberates a gas upon contacting fluid in the conduit, where such compound may include a carbonate, bicarbonate or the like. This segment is extremely effective at clearing the sample-contaminated fluid from conduit 15. The efficiency of the rinsing of the sensor region is greatly enhanced by the introduction of one or more air segments into the second conduit as described. The leading and/or trailing edges of air segments are passed one or more times over the sensors to rinse and re-suspend extraneous material that may have been deposited from the sample. Extraneous material includes any material other than specifically bound analyte or analyte/antibody-enzyme conjugate complex. However, it is an object of the invention that the rinsing is not sufficiently protracted or vigorous as to promote dissociation of specifically bound analyte or analyte/antibody-enzyme conjugate complex from the sensor.

Another advantage of introducing air segments into the fluid is to segment the fluid. For example, after a first segment of the fluid is used to rinse a sensor, a second segment is then placed over the sensor with minimal mixing of the two segments. This feature further reduces background signal from the sensor by more efficiently removing unbound antibody-enzyme conjugate. After the front edge washing, the analysis fluid is pulled slowly until the first air segment is detected at a conductivity sensor. This segment is extremely effective at clearing the sample-contaminated fluid which was mixed in with the first analysis fluid sample. For measurement, a new portion of fluid is placed over the sensors, and the current or potential, as appropriate to the mode of operation, is recorded as a function of time.

Example 2

Figure 12:
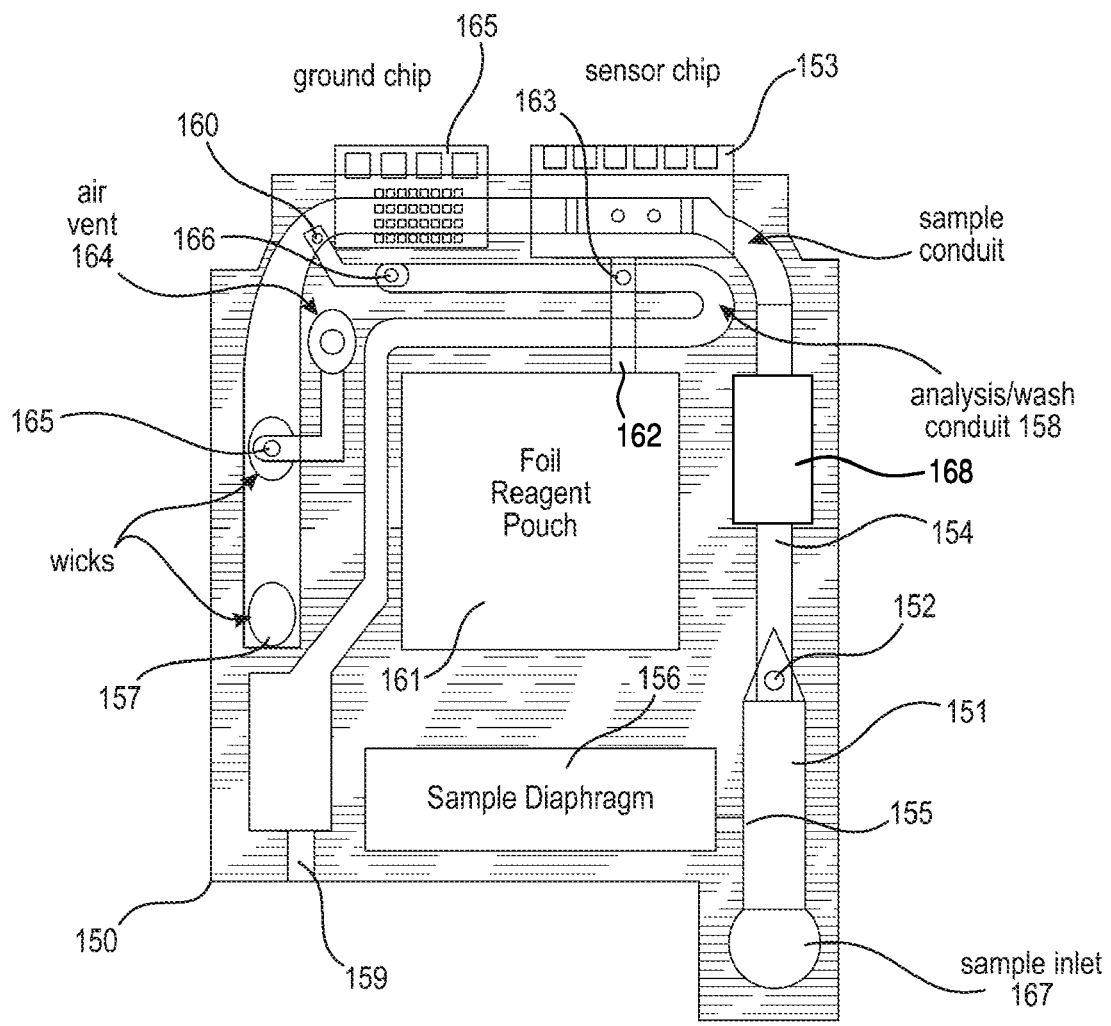
FIG. 12 is a top view of the preferred embodiment of an immunosensor cartridge.

Referring now to FIG. 12, there is shown a top view of an immunosensor cartridge. Cartridge 150 comprises a base and a top portion, preferably constructed of a plastic. The two portions are connected by a thin, adhesive gasket or thin pliable film. As in previous embodiments, the assembled cartridge comprises a sample holding chamber 151 into which a sample containing an analyte of interest is introduced via a sample inlet 167. The sample is amended with opsonized magnetic sacrificial beads and a magnet 168 is used to retain the beads loaded with a target material (e.g., leukocytes) from the sample prior to delivery to the sensor chip 153. A metered portion of the sample is delivered to the sensor chip 153, via the sample conduit 154 (first conduit) as before by the combined action of a capillary stop 152, preferably formed by a 0.012 inch (0.3 mm) laser cut hole in the gasket or film that connects the two portions of the cartridge, and an entry point 155 located at a predetermined point within the sample holding chamber whereby air introduced by the action of a pump means, such as a paddle pushing upon a sample diaphragm 156. After contacting the sensor to permit binding to occur, the sample is moved to vent 157, which contains a wicking material that absorbs the sample and thereby seals the vent closed to the further passage of liquid or air. The wicking material is preferably a cotton fiber material, a cellulose material, or other hydrophilic material having pores. It is important in the present application that the material is sufficiently absorbent (i.e., possesses sufficient wicking speed) that the valve closes within a time period that is commensurate with the subsequent withdrawal of the sample diaphragm actuating means described below, so that sample is not subsequently drawn back into the region of the sensor chip.

As in the specific embodiment shown, there is provided a wash conduit (second conduit) 158, connected at one end to a vent 159 and at the other end to the sample conduit at a point 160 of the sample conduit that is located between vent 157 and sensor chip 153. Upon insertion of the cartridge into a reading apparatus, a fluid is introduced into conduit 158. Preferably, the fluid is present initially within a foil pouch 161 that is punctured by a pin when an actuating means applies pressure upon the pouch. There is also provided a short conduit 162 that connects the fluid to conduit 154 via a small opening in the gasket 163. A second capillary stop initially prevents the fluid from reaching capillary stop 160, so that the fluid is retained within conduit 158.

After vent 157 has closed, the pump is actuated, creating a lowered pressure within conduit 154. Air vent 164, preferably comprising a small flap cut in the gasket or a membrane that vibrates to provide an intermittent air stream, provides a means for air to enter conduit 158 via a second vent 165. The second vent 165 preferably also contains wicking material capable of closing the vent if wetted, which permits subsequent depression of sample diaphragm 156 to close vent 165, if required. Simultaneously with the actuation of sample diaphragm 156, fluid is drawn from conduit 158, through capillary stop 160, into conduit 154. Because the flow of fluid is interrupted by air entering vent 164, at least one air segment (a segment or stream of segments) is introduced.

Further withdrawal of sample diaphragm 156 draws the liquid containing at least one air segment back across the sensing surface of sensor chip 153. The presence of air-liquid boundaries within the liquid enhances the rinsing of the sensor chip surface to remove remaining sample. Preferably, the movement of the sample diaphragm 156 is controlled in conjunction with signals received from the conductivity electrodes housed within the sensor chip adjacent to the analyte sensors. In this way, the presence of liquid over the sensor is detected, and multiple readings can be performed by movement of the fluid in discrete steps.

It is advantageous in this embodiment to perform analyte measurements when only a thin film of fluid coats the sensors, ground chip 165, and a contiguous portion of the wall of conduit 154 between the sensors and ground electrode. A suitable film is obtained by withdrawing fluid by operation of the sample diaphragm 156, until the conductimetric sensor located next to the sensor indicates that bulk fluid is no longer present in that region of conduit 154. It has been found that measurement can be performed at very low (nA) currents, the potential drop that results from increased resistance of a thin film between ground chip and sensor chip (compared to bulk fluid), is not significant.

The ground chip 165 is preferably silver/silver chloride. It is advantageous, to avoid air segments, which easily form upon the relatively hydrophobic silver chloride surface, to pattern the ground chip as small regions of silver/silver chloride interspersed with more hydrophilic regions, such as a surface of silicon dioxide. Thus, a preferred ground electrode configuration comprises an array of silver/silver chloride squares densely arranged and interspersed with silicon dioxide. There is a further advantage in the avoidance of unintentional segments if the regions of silver/silver chloride are somewhat recessed.

Figure 13:
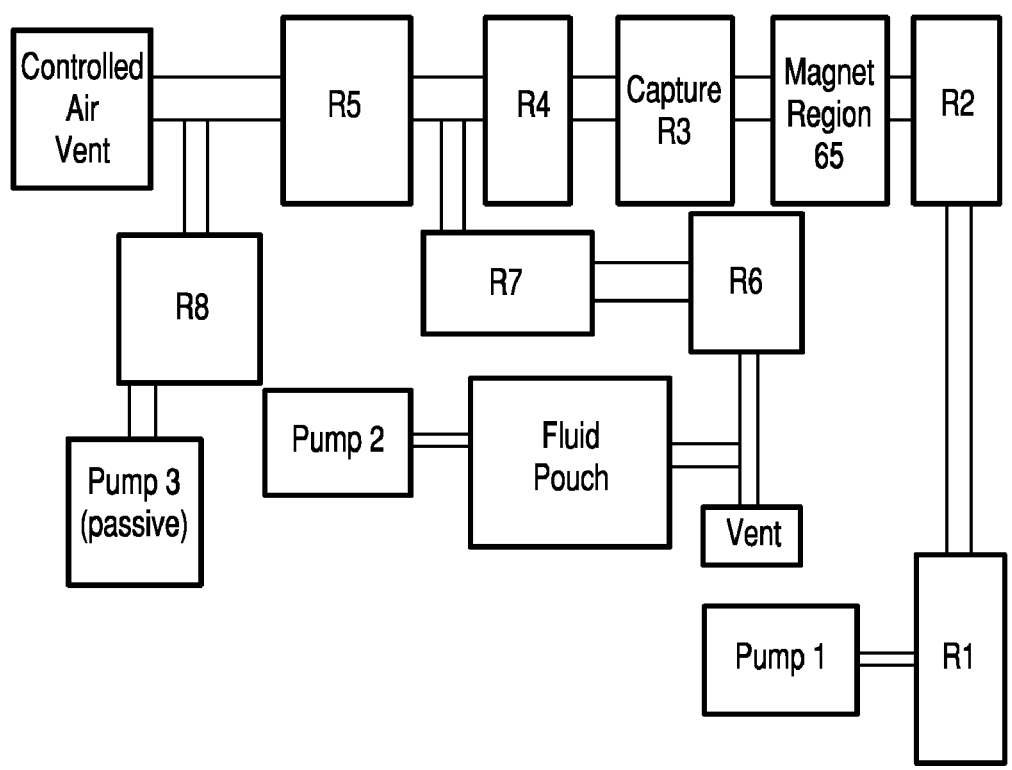
FIG. 13 is a schematic view of the fluidics of a preferred embodiment of an immunosensor cartridge.

Referring now to FIG. 13, there is shown a schematic view of the fluidics of the preferred embodiment of an immunosensor cartridge. Regions R1-R8 represent specific regions of the conduits associated with specific operational functions. Thus R1 represents the sample holding chamber and R2 represents the sample conduit whereby a metered portion of the sample containing leukocytes is transferred to the capture region. The sample may be amended with a substance, e.g., opsonized magnetic sacrificial beads, coated upon the walls of the either R1 or R2. As discussed above, the beads preferably are opsonized for leukocytes and bind upon dissolution into the sample. In magnet region 65, a magnet is used to magnetically retain the magnetic beads and associated leukocytes from the sample substantially out of contact with an immunosensor. R3 represents the capture region, which houses the conductimetric and analyte sensors. R4 and R5 represent portions of the first conduit that are optionally used for further amendment of fluids with substances coated onto the conduit wall, whereby more complex assay schemes are achieved; R6 represents the portion of the second conduit into which fluid is introduced upon insertion of the cartridge into a reading apparatus. R7 comprises a portion of the conduit located between capillary stops 160 and 166, in which further amendment can occur. R8 represents the portion of conduit 154 located between point 160 and vent 157, and which can further be used to amend liquids contained within.

Embodiments of the present invention are applicable to samples where residual leukocytes may be present despite an intention to remove them by centrifugation or filtration, e.g., plasma. Certain embodiments are also applicable to samples that may have been diluted, e.g., with a buffer. Furthermore, while the invention is generally directed to amending the sample by dissolving into the sample a dry reagent, it is also practical in other embodiments to add the reagent, e.g., the magnetic sacrificial beads, as a liquid to the sample during the analysis or during sample collection. Additionally, it is intended that the scope of the present invention be limited solely by the scope of the following claims.

What is claimed is:

1. A cartridge for performing a competitive immunoassay for a sample analyte suspected of being present in a blood sample containing leukocytes, the cartridge comprising:
   a sample inlet for receiving the blood sample;
   a metering chamber for metering the blood sample to form a metered sample;
   one or more dry reagent coating layers within the cartridge comprising magnetic beads opsonized to leukocytes and a labeled analyte, wherein the opsonized magnetic beads are present in an amount in excess of the leukocytes in the blood sample sufficient to substantially sequester any leukocytes present in the sample;
   an electrode comprising an immobilized antibody to the sample analyte and to the labeled analyte; and
   one or more pumping elements for moving the metered sample and the labeled analyte to the electrode.

2. The cartridge of claim 1, further comprising a magnet in the cartridge for positioning the magnetic beads.

3. A cartridge for performing a non-competitive immunoassay for a sample analyte suspected of being present in a blood sample containing leukocytes, the cartridge comprising:
   a sample inlet for receiving the blood sample;
   a metering chamber for metering the blood sample to form a metered sample;
   one or more dry reagent coating layers within the cartridge comprising magnetic beads opsonized to leukocytes and a signal antibody to the analyte, wherein the opsonized magnetic beads are present in an amount in excess of the leukocytes in the blood sample sufficient to substantially sequester any leukocytes present in the sample;
   an electrode comprising an immobilized antibody to the sample analyte; and
   one or more pumping elements for moving the metered sample to the electrode.

4. The cartridge of claim 3, further comprising a magnet in the cartridge for positioning the magnetic beads.

5. A kit for performing an analyte immunoassay in a whole blood sample, comprising:
   magnetic beads opsonized to leukocytes, wherein the magnetic beads are movable by a magnetic field, and wherein magnetic beads are present in an amount in excess of the leukocytes in the blood sample sufficient to substantially sequester any leukocytes present in the sample;

a magnet in the cartridge for retaining the magnetic beads; and an immunosensor, wherein leukocytes in the whole blood sample bind to said magnetic beads, and wherein the magnetic field is capable of retaining at least a portion of said magnetic beads out of contact from said immunosensor.

6. The kit of claim 5, wherein the immunoassay is a sandwich assay.

7. The kit of claim 5, wherein the immunoassay is a competitive assay.

8. The kit of claim 5, wherein the kit further comprises an anticoagulant.

9. The kit of claim 5, wherein the magnetic beads comprise a magnetite ($Fe_3O_4$) core coated with a styrene-acrylic acid copolymer.

10. The kit of claim 5, wherein the magnetic beads comprise magnetic beads coated with non-human IgG or fragments thereof.

11. The kit of claim 5, wherein the magnetic beads have an average particle size of from 0.01 µm to 20 µm.

12. The kit of claim 5, wherein the magnetic beads have an average particle size of from 0.1 µm to 5 µm.

13. The kit of claim 5, wherein the magnetic beads have an average particle size of from 3 µm to 5 µm.

14. The kit of claim 5, wherein the magnetic beads are in one or more dissolvable dry reagent coatings in the cartridge.

15. The kit of claim 5, wherein the magnet is a permanent magnet.

16. The kit of claim 5, wherein the magnet is an electromagnet.

17. The kit of claim 5, wherein at least 50 wt. % of the magnetic beads are retained out of contact from the immunosensor.

18. The kit of claim 5, wherein at least 75 wt. % of the magnetic beads are retained out of contact from the immunosensor.

19. A cartridge for performing a competitive immunoassay for a sample analyte suspected of being present in a blood sample containing leukocytes, the cartridge comprising:

a sample inlet for receiving the blood sample;

a metering chamber for metering the blood sample to form a metered sample;

one or more dry reagent coating layers on the cartridge comprising magnetic beads opsonized to leukocytes and a labeled analyte, wherein the magnetic beads are present in an amount sufficient to provide a dissolved bead concentration of at least 5 micrograms per microliter of sample which is an amount in excess of the leukocytes in the blood sample sufficient to substantially sequester any leukocytes present in the sample;

an electrode comprising an immobilized antibody to the sample analyte and to the labeled analyte; and one or more pumping elements for moving the metered sample and the labeled analyte to the electrode.

20. The cartridge of claim 19, wherein the magnetic beads are present in an amount sufficient to provide a dissolved bead concentration of at least 10 micrograms per microliter of sample.

21. The cartridge of claim 19, wherein the magnetic beads are present in an amount sufficient to provide a dissolved bead concentration of at least 15 micrograms per microliter of sample.

* * * * *